United States Patent
Nishimura et al.

(10) Patent No.: US 7,271,153 B2
(45) Date of Patent: Sep. 18, 2007

(54) NITROGENOUS HETEROCYCLIC DERIVATIVES, MEDICINAL COMPOSITIONS CONTAINING THE SAME, MEDICINAL USES THEREOF, AND INTERMEDIATES THEREFOR

(75) Inventors: Toshihiro Nishimura, Hotaka-machi (JP); Hideki Fujikura, Matsumoto (JP); Nobuhiko Fushimi, Matsumoto (JP); Kazuya Tatani, Matsumoto (JP); Kenji Katsuno, Tatsuno-machi (JP); Masayuki Isaji, Shiojiri (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/481,013

(22) PCT Filed: Jun. 17, 2002

(86) PCT No.: PCT/JP02/06000

§ 371 (c)(1),
(2), (4) Date: Aug. 20, 2004

(87) PCT Pub. No.: WO03/000712

PCT Pub. Date: Jan. 3, 2003

(65) Prior Publication Data

US 2005/0049203 A1    Mar. 3, 2005

(30) Foreign Application Priority Data

Jun. 20, 2001   (JP)   ............................. 2001-187368

(51) Int. Cl.
*A01N 43/04*   (2006.01)
*A61K 31/70*   (2006.01)
*C07H 15/24*   (2006.01)

(52) U.S. Cl. .................. 514/27; 514/25; 514/866; 514/909; 536/4.1; 536/18.1

(58) Field of Classification Search .............. 514/25, 514/27, 866, 844, 909; 536/4.1, 18.1
See application file for complete search history.

(56) References Cited

U.S. PATENT DOCUMENTS

| 4,248,999 | A | 2/1981 | Baba et al. | |
| 6,683,056 | B2 * | 1/2004 | Washburn et al. | 514/25 |
| 2005/0049203 | A1 * | 3/2005 | Nishimura et al. | 514/23 |

FOREIGN PATENT DOCUMENTS

| GB | 1 541 185 | 2/1979 |
| JP | 53-135987 | 11/1978 |
| JP | 53-144582 | 12/1978 |
| JP | 10-182688 A | 7/1998 |
| JP | 2000-44589 A | 2/2000 |

OTHER PUBLICATIONS

Lutz Eggers, et al., 4-Alkyl-and 4-Benzyl-Substituted 3,3'-Oxybispyridines: An Efficient Synthesis at Room Temperature; Synthesis; Jun. 1996; pp. 763-768.

Alan R. Katritzky, et al.; 1,3-Dipolar Character of Six-membered Aromatic Rings. Part 52.$^1$ 2π+8π Cycloaddition Reactions of 1-Substituted 3-Oxidopyridinium Betaines; J.Chem.Soc., Perkin Trans 1, 1980, No. 5, pp. 1176-1184.

Lewis A. Walter, et al.; Derivatives of 3-Piperidinol as Central Stimulants; J. Med. Chem. Jul. 1968, vol. 11, No. 4; pp. 792-796.

Kenji Tsujihara, et al.; Na$^+$-Glucose Cotransporter (SGLT) Inhibitors as Antidiabetic Agents. 4. Synthesis and Pharmacological Properties of 4'-Dehydroxyphlorizin Derivatives Substituted on the B Ring; J Med. Chem. 1999, vol. 42, No. 26, pp. 5311-5324; Dec. 1999.

* cited by examiner

Primary Examiner—Shaojia Anna Jiang
Assistant Examiner—Traviss McIntosh
(74) Attorney, Agent, or Firm—Sughrue Mion, PLLC

(57) ABSTRACT

The present invention provides nitrogen-containing heterocyclic derivatives represented by the general formula:

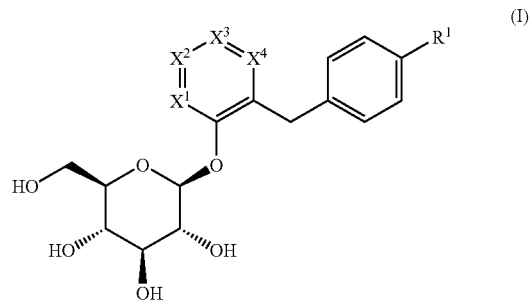

wherein $X^1$ and $X^3$ independently represent N or CH; $X^2$ represents N or $CR^2$; $X^4$ represents N or $CR^3$; and with the proviso that one or two of $X^1$, $X^2$, $X^3$ and $X^4$ represent N; $R^1$ represents a hydrogen atom, a halogen atom, a lower alkyl group, a lower alkoxy group, a lower alkylthio group, a lower alkoxy-substituted (lower alkyl) group, a lower alkoxy-substituted (lower alkoxy) group, a lower alkoxy (lower alkoxy)-substituted (lower alkyl) group, a cyclic lower alkyl group, a halo(lower alkyl) group or a group represented by the general formula: HO-A- wherein A represents a lower alkylene group, a lower alkyleneoxy group or a lower alkylenethio group; $R^2$ represents a hydrogen atom, a halogen atom, a lower alkyl group, a cyclic lower alkyl group, a lower alkoxy group, an amino group, a (lower acyl)amino group, a mono(lower alkyl)amino group or a di(lower alkyl)amino group; and $R^3$ represents a hydrogen atom or a lower alkyl group, or pharmaceutically acceptable salts thereof, or prodrugs thereof which are useful as agents for the prevention or treatment of a disease associated with hyperglycemia such as diabetes, diabetic complications or obesity, pharmaceutical compositions comprising the same, and pharmaceutical uses and production intermediates thereof.

7 Claims, No Drawings

```
                          SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 1
atggaggagc acacagaggc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 2
ggcatagaag ccccagagga                                              20

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 3
aacctcgaga tggaggagca cacagaggc                                    29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 4
aacaagcttg gcatagaagc cccagagga                                    29

<210> SEQ ID NO 5
<211> LENGTH: 25
<212> TYPE: PRT
<213> ORGANISM: Artificial Sequence
<220> FEATURE:
<223> OTHER INFORMATION: peptide fused to the carboxyl
      terminal alanine residue of human SGLT2

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25
```

NITROGENOUS HETEROCYCLIC DERIVATIVES, MEDICINAL COMPOSITIONS CONTAINING THE SAME, MEDICINAL USES THEREOF, AND INTERMEDIATES THEREFOR

TECHNICAL FIELD

The present invention relates to nitrogen-containing heterocyclic derivatives or pharmaceutically acceptable salts thereof, or prodrugs thereof which are useful as medicaments, pharmaceutical compositions comprising the same, pharmaceutical uses thereof and production intermediates thereof.

More particularly, the present invention relates to nitrogen-containing heterocyclic derivatives represented by the general formula:

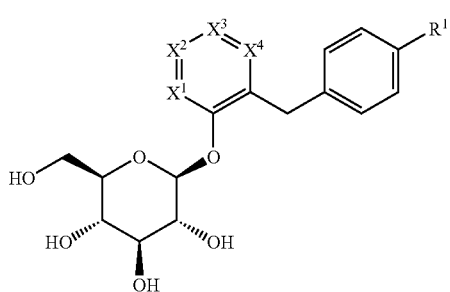

wherein $X^1$ and $X^3$ independently represent N or CH; $X^2$ represents N or $CR^2$; $X^4$ represents N or $CR^3$; and with the proviso that one or two of $X^1$, $X^2$, $X^3$ and $X^4$ represent N; $R^1$ represents a hydrogen atom, a halogen atom, a lower alkyl group, a lower alkoxy group, a lower alkyl thio group, a lower alkoxy-substituted (lower alkyl) group, a lower alkoxy-substituted(lower alkoxy) group, a lower alkoxy (lower alkoxy)-substituted (lower alkyl) group, a cyclic lower alkyl group, a halo(lower alkyl) group or a group represented by the general formula: HO-A—wherein A represents a lower alkylene group, a lower alkyleneoxy group or a lower alkylenethio group; $R^2$ represents a hydrogen atom, a halogen atom, a lower alkyl group, a cyclic lower alkyl group, a lower alkoxy group, an amino group, a (lower acyl)amino group, a mono(lower alkyl)amino group or a di(lower alkyl)amino group; and $R^3$ represents a hydrogen atom or a lower alkyl group, or pharmaceutically acceptable salts thereof, or prodrugs thereof which exhibit an inhibitory activity in human SGLT2 and are useful as agents for the prevention or treatment of a disease associated with hyperglycemia such as diabetes, diabetic complications or obesity, pharmaceutical compositions comprising the same, and pharmaceutical uses and production intermediates thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and insulin sensitivity enhancers have been employed as antidiabetic agents. However, biguanides and sulfonylureas show occasionally adverse effects such as lactic acidosis and hypoglycemia, respectively. Insulin sensitivity enhancers show occasionally adverse effects such as edema, and are concerned for advancing obesity. Therefore, in order to solve these problems, it has been desired to develop antidiabetic agents having a new mechanism.

In recent years, research and development of new type antidiabetic agents have been progressing, which promote urinary glucose excretion and lower blood glucose level by preventing reabsorption of excess glucose at the kidney (J. Clin. Invest., Vol. 79, pp. 1510-1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397-404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents which have a potent inhibitory activity in human SGLT2 and have a new mechanism has been desired. In addition, since such agents for promoting the excretion of urinary glucose excrete excess glucose though the urine and consequently the glucose accumulation in the body is decreased, they are also expected to have a preventing or alleviating effect on obesity and a diuretic effect. Furthermore, the agents are considered to be useful for various related diseases which occur accompanying the progress of diabetes or obesity due to hyperglycemia.

DISCLOSURE OF THE INVENTION

The present inventors have studied earnestly to find compounds having an inhibitory activity in human SGLT2. As a result, it was found that compounds represented by the above general formula (I) show an excellent inhibitory activity in human SGLT2, thereby forming the basis of the present invention.

The present invention is to provide the above nitrogen-containing heterocyclic derivatives, pharmaceutically acceptable salts thereof or prodrugs thereof which exert an inhibitory activity in human SGLT2 and show an excellent hypoglycemic effect by excreting excess glucose in the urine through preventing the reabsorption of glucose at the kidney, pharmaceutical compositions comprising the same, and pharmaceutical uses thereof and production intermediates thereof.

This is, the present invention relates to a nitrogen-containing heterocyclic derivative represented by the general formula:

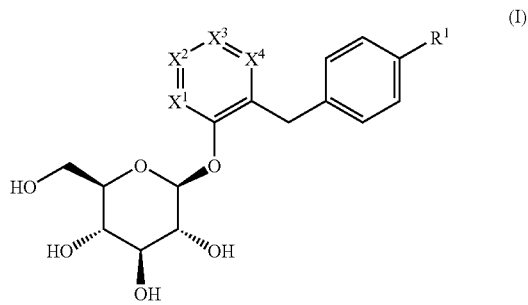

wherein $X^1$ and $X^3$ independently represent N or CH; $X^2$ represents N or $CR^2$; $X^4$ represents N or $CR^3$; and with the proviso that one or two of $X^1$, $X^2$, $X^3$ and $X^4$ represent N; $R^1$ represents a hydrogen atom, a halogen atom, a lower alkyl group, a lower alkoxy group, a lower alkylthio group, a lower alkoxy-substituted (lower alkyl) group, a lower alkoxy-substituted(lower alkoxy) group, a lower alkoxy(lower alkoxy)-substituted (lower alkyl) group, a cyclic lower alkyl group, a halo(lower alkyl) group or a group represented by the general formula: HO-A- wherein A represents a lower alkylene group, a lower alkyleneoxy group or a lower alkylenethio group; $R^2$ represents a hydrogen atom, a halogen atom, a lower alkyl group, a cyclic lower alkyl group, a lower alkoxy group, an amino group, a (lower acyl)amino group, a mono(lower alkyl)amino group or a di(lower alkyl)amino group; and $R^3$ represents a hydrogen atom or a lower alkyl group, a pharmaceutically acceptable salt thereof or a prodrug thereof.

Also, the present invention relates to a pharmaceutical composition, a human SGLT2 inhibitor and an agent for the prevention or treatment of a disease associated with hyperglycemia, which comprise as an active ingredient a nitrogen-containing heterocyclic derivative represented by the above general formula (I), a pharmaceutically acceptable salt thereof or a prodrug thereof.

The present invention relates to a method for the prevention or treatment of a disease associated with hyperglycemia, which comprises administering an effective amount of a nitrogen-containing heterocyclic derivative represented by the above general formula (I), a pharmaceutically acceptable salt thereof or a prodrug thereof.

The present invention relates to a use of a nitrogen-containing heterocyclic derivative represented by the above general formula (I), a pharmaceutically acceptable salt thereof or a prodrug thereof for the manufacture of a pharmaceutical composition for the prevention or treatment of a disease associated with hyperglycemia.

The present invention relates to a pharmaceutical combination which comprises (A) a nitrogen-containing heterocyclic derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxy-methyl-glutaryl coenzyme A reductase inhibitor, a fibric acid derivative, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

The present invention relates to a method for the prevention or treatment of a disease associated with hyperglycemia, which comprises administering an effective amount of (A) a nitrogen-containing heterocyclic derivative represented by the above general formula (I), a pharmaceutically acceptable salt thereof or a prodrug thereof, in combination with (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

The present invention relates to a use of (A) a nitrogen-containing heterocyclic derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia.

Furthermore, the present invention relates to a nitrogen-containing heterocyclic derivative represented by the general formula:

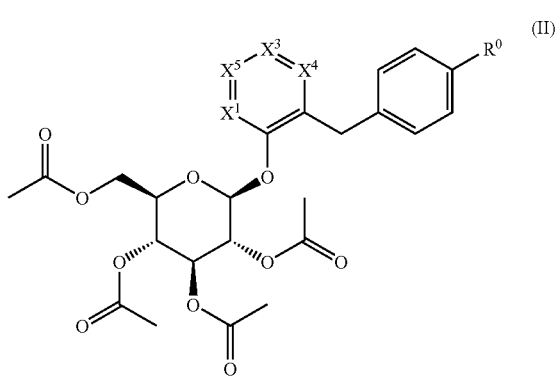

(II)

wherein $X^1$ and $X^3$ independently represent N or CH; $X^4$ represents N or $CR^3$; $X^5$ represents N or $CR^4$; and with the proviso that one or two of $X^1$, $X^3$, $X^4$ and $X^5$ represent N; $R^0$ represents a hydrogen atom, a halogen atom, a lower alkyl group, a lower alkoxy group, a lower alkylthio group, or a lower alkoxy-substituted (lower alkyl) group, a lower alkoxy-substituted (lower alkoxy) group, a lower alkoxy (lower alkoxy)-substituted (lower alkyl) group, a cyclic lower alkyl group, a halo(lower alkyl) group or a group represented by the general formula: $P^{10}$—O-A- wherein $P^{10}$ represents a hydrogen atom or a hydroxy-protective group; and A represents a lower alkylene group, a lower alkyleneoxy group or a lower alkylenethio group; $R^3$ represents a hydrogen atom or a lower alkyl group; and $R^4$ represents a hydrogen atom, a halogen atom, a lower alkyl group, a cyclic lower alkyl group, a lower alkoxy group, an amino group which may have a protective group, a (lower acyl) amino group, a mono (lower alkyl) amino group which may have a protective group or a di(lower alkyl)amino group, or salts thereof, and a nitrogen-containing heterocyclic derivative represented by the general formula:

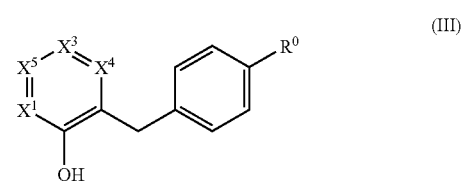

(III)

wherein $X^1$ and $X^3$ independently represent N or CH; $X^4$ represents N or $CR^3$; $X^5$ represents N or $CR^4$; and with the proviso that one or two of $X^1$, $X^3$, $X^4$ and $X^5$ represent N; $R^0$ represents a hydrogen atom, a halogen atom, a lower alkyl group, a lower alkoxy group, a lower alkylthio group, or a lower alkoxy-substituted (lower alkyl) group, a lower alkoxy-substituted (lower alkoxy) group, a lower alkoxy (lower alkoxy)-substituted (lower alkyl) group, a cyclic lower alkyl group, a halo(lower alkyl) group or a group represented by the general formula: $P^{10}$—O-A- wherein $P^{10}$ represents a hydrogen atom or a hydroxy-protective group; and A represents a lower alkylene group, a lower alkyleneoxy group or a lower alkylenethio group; $R^3$ represents a hydrogen atom or a lower alkyl group; and $R^4$ represents a hydrogen atom, a halogen atom, a lower alkyl group, a cyclic lower alkyl group, a lower alkoxy group, an amino group which may have a protective group, a (lower acyl) amino group, a mono (lower alkyl) amino group which may have a protective group or a di (lower alkyl) amino group, or salts thereof.

In the present invention, the term "prodrug" means a compound which is converted into a nitrogen-containing heterocyclic derivative represented by the above general formula (I) as an active form thereof in vivo. As prodrugs of a nitrogen-containing heterocyclic derivative represented by the above general formula (I) or pharmaceutically acceptable salts, for example, a compound represented by the general formula:

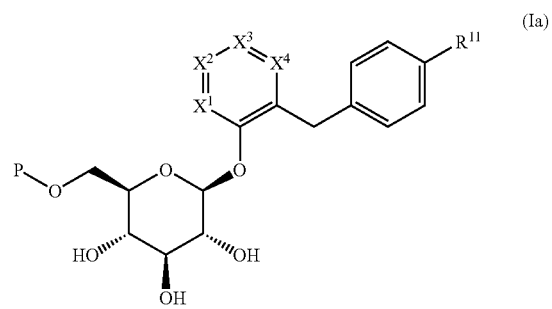

(Ia)

wherein P represents a hydrogen atom or a group forming a prodrug; $X^1$ and $X^3$ independently represent N or CH; $X^2$ represents N or $CR^2$; $X^4$ represents N or $CR^3$; and with the proviso that one or two of $X^1$, $X^2$, $X^3$ and $X^4$ represent N; $R^2$ represents a hydrogen atom, a halogen atom, a lower alkyl group, a cyclic lower alkyl group, a lower alkoxy group, an amino group, a (lower acyl)amino group, a mono (lower alkyl)amino group or a di(lower alkyl)amino group; $R^3$ represents a hydrogen atom or a lower alkyl group; $R^{11}$ represents a hydrogen atom, a halogen atom, a lower alkyl group, a lower alkoxy group, a lower alkylthio group, a lower alkoxy-substituted (lower alkyl) group, a lower alkoxy-substituted (lower alkoxy) group, a lower alkoxy (lower alkoxy)-substituted (lower alkyl) group, a cyclic lower alkyl group, a halo(lower alkyl) group or a group represented by the general formula: $P^1$—O-A- wherein $P^1$ represents a hydrogen atom or a group forming a prodrug; and A represents a lower alkylene group, a lower alkyleneoxy group or a lower alkylenethio group; and with the proviso that at least one of P and $R^{11}$ having a group forming a prodrug, or a pharmaceutically acceptable salt thereof are illustrated.

As examples of groups forming prodrugs, a hydroxy-protective group which can be used generally in a prodrug such as a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group are illustrated. Of the compounds of the present invention, in a prodrug, a group forming a prodrug may be at any hydroxy group, and two or more such groups are acceptable.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "lower alkylene group" means a straight-chained or branched alkylene group having 1 to 6 carbon atoms such as a methylene group, an ethylene group, a trimethylene group a propylene group or the like; the term "lower alkyleneoxy group" means a hydroxy group substituted by the above lower alkylene group; and the term "lower alkylenethio group" means a thiol group substituted by the above lower alkylene group. The term "cyclic lower alkyl group" means a 3- to 7-member cyclic alkyl group such as a cyclopropyl group, a cyclobutyl group, a cyclopentyl group, a cyclohexyl group, a cycloheptyl group or the like. The term "halogen atom" means a fluorine atom, a chlorine atom, a bromine atom or an iodine atom; and the term "halo(lower alkyl) group" means the above lower alkyl group substituted by 1 to 3 different or same halogen atoms defined above. The term "lower acyl group" means a straight-chained or branched acyl group having 2 to 7 carbon atoms or a cyclic acyl group having 4 to 8 carbon atoms such as an acetyl group, a propionyl group, a butyryl group, an isobutyryl group, a pivaloyl group, a hexanoyl group, a cyclohexylcarbonyl group or the like; and the term "lower alkoxy-substituted (lower acyl) group means the above lower acyl group substituted by the above lower alkoxy group. The term "lower alkoxy-substituted (lower alkoxy) group" means the above lower alkoxy group substituted by the above lower alkoxy group; the term "lower alkoxy-substituted (lower alkyl) group" means the above lower alkyl group substituted by the above lower alkoxy group; and the term "lower alkoxy(lower alkoxy)-substituted (lower alkyl) group" means the above alkyl group substituted by the above lower alkoxy-substituted (lower alkoxy) group. The term "lower alkoxycarbonyl group" means a straight-chained or branched alkoxycarbonyl group having 2 to 7 carbon atoms or a cyclic alkoxycarbonyl group having 4 to 8 carbon atoms such as a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isopentyloxycarbonyl group, a neo-pentyloxycarbonyl group, a tert-pentyloxycarbonyl group, a hexyloxycarbonyl group, and a cyclohexyloxycarbonyl group; the term "lower alkoxycarbonyl-substituted (lower acyl) group means the above lower acyl group substituted by the above lower alkoxycarbonyl group such as a 3-(ethoxycarbonyl)propionyl group; and the term "lower alkoxy-substituted (lower alkoxycarbonyl) group means the above lower alkoxycarbonyl group substituted by the above alkoxy group such as a 2-methoxyethoxycarbonyl group. The term "mono(lower alkyl)amino group" means an amino group mono-substituted by the above lower alkyl group; the term "di(lower alkyl)amino group" means an amino group di-substituted by the same or different lower alkyl group defined above; and the term "(lower acyl)amino group" means an amino group substituted by the above lower acyl group. In a various production intermediate, the term "hydroxy-protective group" means a hydroxy-protective group used in general organic synthesis in addition to a hydroxy-protective group used in general in the above prodrug, and specifically a benzyl group, a methyl group, a methoxymethyl group, an acetyl group, a benzoyl group, 2-trimethyl-silylethoxymethyl group and the like can be illustrated. In a various production intermediate, the term "amino-protective group" means an amino-protective group used in general organic synthesis such as a benzyl group, a p-methoxybenzyl group, a lower acyl group, a lower alkoxycarbonyl group or the like.

The term "nitrogen-containing heterocyclic derivative" represented by the above general formula (I), (II) and (III) means a 3-benzyl-2-hydroxypyridine derivative, a 4-benzyl-3-hydroxypyridine derivative, a 3-benzyl-4-hydroxypyridine derivative, a 2-benzyl-3-hydroxypyridine derivative, a 4-benzyl-3-hydroxypyridazine derivative, a 4-benzyl-5-hydroxypyridazine derivative, a 3-benzyl-4-hydroxypyridazine derivative, a 5-benzyl-4-hydroxypyrimidine derivative, a 4-benzyl-5-hydroxypyrimidine derivative, or a 2-benzyl-3-hydroxypyrazine derivative. In cases that there are tautomers in the present compounds, the present invention includes all tautomers.

The nitrogen-containing heterocyclic derivatives represented by the above general formula (I) of the present invention and prodrugs thereof can be prepared, for example, according to the reactions described by the following Scheme 1:

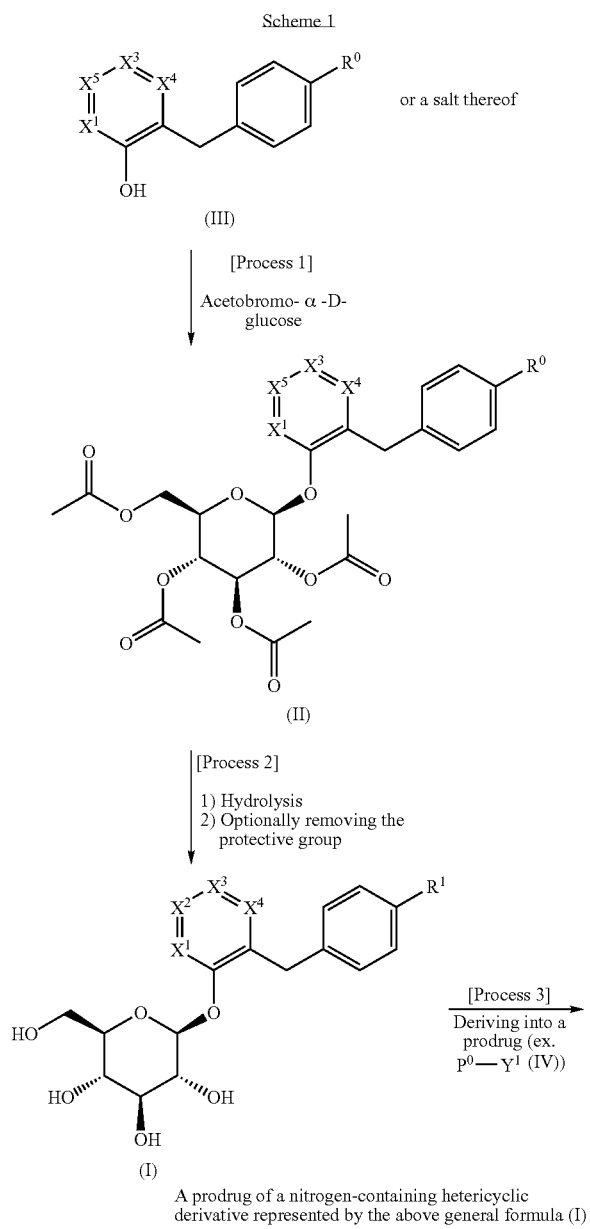

wherein $P^0$ represents a group forming a prodrug; $Y^1$ represents a leaving group such as a chlorine atom, a bromine atom or the like; and $X^1$, $X^2$, $X^3$, $X^4$, $X^5$, $R^0$ and $R^1$ have the same meanings as defined above.

Process 1

A corresponding compound represented by the above general formula (II) can be prepared by subjecting an alcohol compound or a salt thereof to glycosidation using acetobromo-α-D-glucose in the presence of a base such as a silver salt like silver carbonate, silver oxide or the like or a base such as potassium carbonate, sodium hydride or the like in an inert, solvent. As the solvent used in the glycosidation reaction, for example, acetonitrile, tetrahydrofuran, dichloromethane, toluene, N,N-dimethylformamide, a mixed solvent and the like can be illustrated. The reaction temperature is usually from room temperature to reflux temperature, and the reaction time is usually from 2 hours to 2 days, varying based on a used starting material, solvent and reaction temperature.

Process 2

A nitrogen-containing heterocyclic derivative represented by the above general formula (I) of the present invention can be prepared by subjecting a compound represented by the above general formula (II) to alkaline hydrolysis and optionally removal of a protective group in the usual way. As the solvent used in the alkaline hydrolysis, methanol, ethanol, tetrahydrofuran, water, a mixed solvent thereof and the like can be illustrated, and as the base used, sodium hydroxide, potassium hydroxide, sodium methoxide, sodium ethoxide and the like can be illustrated. The reaction temperature is usually from 0° C. to room temperature, and the reaction time is usually from 30 minutes to 6 hours, varying based on a used starting material, solvent and reaction temperature.

Process 3

A prodrug of a nitrogen-containing heterocyclic derivative represented by the above general formula (I) (for example, a prodrug represented by the above general formula (Ia)) can be prepared by introducing hydroxy-protective groups generally capable for use in a prodrug into hydroxy groups of a nitrogen-containing heterocyclic derivative represented by the above general formula (I) using, for example, an agent for introducing a hydroxy-protective group represented by the above general formula (IV) in the usual way.

For example, a compound represented by the above general formula (III) as a starting material in the above production method (Scheme 1) can be prepared according to the reaction described in the following Scheme 2:

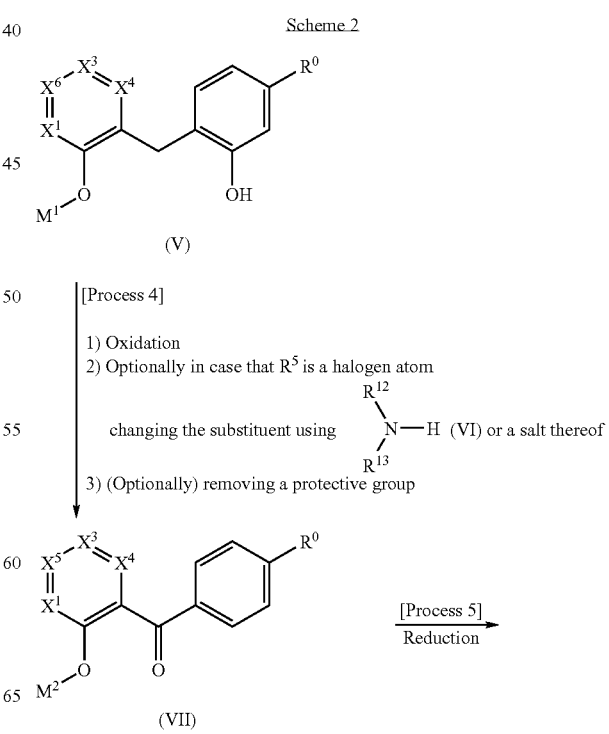

-continued

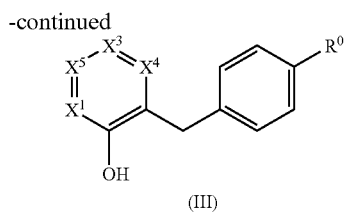

(III)

wherein $M^1$ represents a hydroxy-protective group; $M^2$ represents a hydrogen atom or a hydroxy-protective group; $X^6$ represents N or $CR^5$; $R^5$ represents a hydrogen atom, a halogen atom, a lower alkyl group, a cyclic lower alkyl group or a lower alkoxy group; $R^{12}$ represents a hydrogen atom, a lower alkyl group or an amino-protective group; $R^{13}$ represents a hydrogen atom or a lower alkyl group; and $X^1$, $X^3$, $X^4$, $X^5$ and $R^0$ have the same meanings as defined above, and with the proviso that one or two of $X^1$, $X^3$, $X^4$ and $X^6$ of a compound (V) represent N.

Process 4

A compound represented by the above general formula (VII) can be prepared by subjecting a compound represented by the above general formula (V) to oxidation using a Dess-Martin reagent in an inert solvent and optionally removal of the protective group in the usual way. As the solvent used in the oxidation, for example, dichloromethane, chloroform, a mixed solvent thereof or the like can be illustrated. The reaction temperature is usually from 0° C. to reflux temperature, and the reaction time is usually from 10 minutes to 1 day, varying based on a used starting material, solvent and reaction temperature. In addition, in case that $R^5$ is a halogen atom, a corresponding compound can be derived optionally by subjecting such a compound to substitution reaction using an amine derivative represented by the above general formula (VI) or a salt thereof in the presence or absence of a base such as sodium carbonate, potassium carbonate, sodium hydrogen carbonate or the like, in or without a solvent. As the solvent used in the substitution reaction, N,N-dimethylformamide, N,N-dimethylacetoamide, tetrahydro-furan, tert-butanol, a mixed solvent thereof or the like can be illustrated. The reaction temperature is usually from room temperature to 150° C., and the reaction time is usually from 1 hour to 1 day, varying based on a used starting material, solvent and reaction temperature.

Process 5

A compound represented by the above general formula (III) can be prepared by subjecting a compound represented by the above general formula (VII) to 1) hydrogenation in the presence or absence of an acid such as hydrochloric acid using a palladium catalyst such as palladium-carbon powder or the like in an inert solvent under a hydrogen atmosphere, or to 2) reduction using a reducing agent. As the solvent used in the 1) hydrogenation, for example, methanol, ethanol, tetrahydrofuran, ethyl acetate, acetic acid, isopropanol, a mixed solvent thereof or the like can be illustrated. The reaction temperature is usually from 0° C. to reflux temperature, and the reaction time is usually from 30 minutes to 1 day, varying based on a used starting material, solvent and reaction temperature. The 2) reduction using a reducing agent can be performed in the presence of a Lewis acid such as trifluoroborate or the like using a reducing agent such as sodium cyanoborohydride or the like in an inert solvent such as tetrahydrofuran. The reaction temperature is usually from room temperature to reflux temperature, and the reaction time is usually from 1 hour to 1 day, varying based on a used starting material, solvent and reaction temperature.

Of compounds represented by the above general formula (III) as a starting material in the above production method (Scheme 1), a compound represented by the following general formula (IIIa) can be also prepared, for example, according to the reaction described in the following Scheme 3:

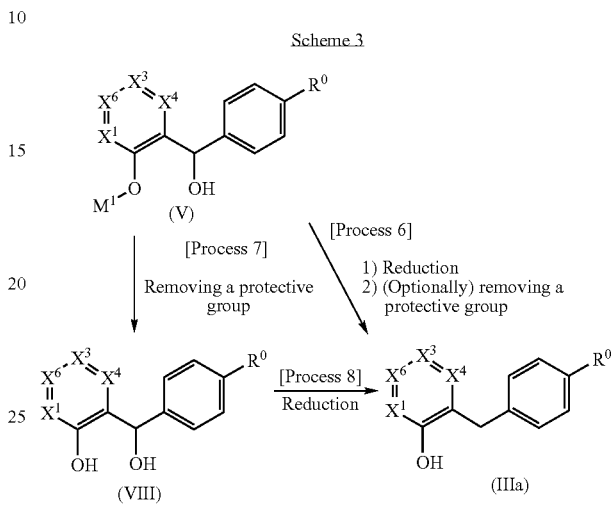

wherein $M^1$, $X^1$, $X^3$, $X^4$, $X^6$ and $R^0$ have the same meanings as defined above.

Process 6

A compound represented by the general formula (IIIa) can be prepared by subjecting a compound represented by the above general formula (V) to hydrogenation in the presence or absence of an acid such as hydrochloric acid using a palladium catalyst such as palladium-carbon powder in an inert solvent under a hydrogen atmosphere, and optionally to removal of a protective group in the usual way. As the solvent used in the hydrogenation, for example, methanol, ethanol, tetrahydrofuran, ethyl acetate, acetic acid, isopropanol, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 7

A compound represented by the above general formula (VIII) can be prepared by removing the protective group $M^1$ of a compound represented by the above general formula (V) in the usual way.

Process 8

A compound represented by the above general formula (IIIa) can be prepared by subjecting a compound represented by the above general formula (VIII) to hydrogenation in the presence or absence of an acid such as hydrochloric acid using a palladium catalyst such as palladium-carbon powder in an inert solvent under a hydrogen atmosphere. As the solvent used in the hydrogenation, for example, methanol, ethanol, tetrahydrofuran, ethyl acetate, acetic acid, isopropanol, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Of compounds represented by the above general formula (III) as a starting material in the above production method (Scheme 1), a compound represented by the following general formula (IIIb) can be prepared, for example, according to the reaction described in the following Scheme 4:

Scheme 4

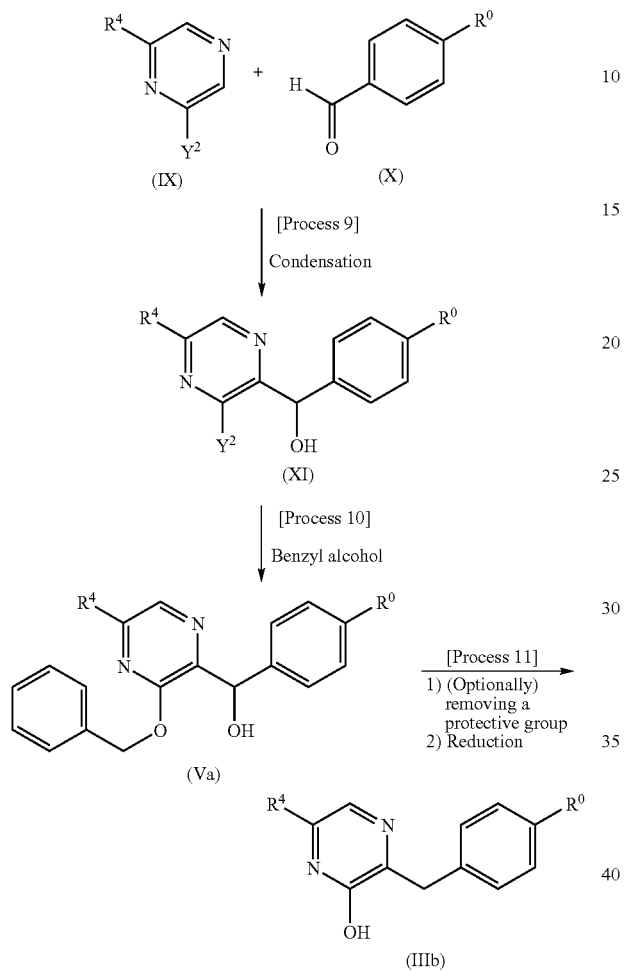

wherein $Y^2$ represents a chlorine atom or a bromine atom; and $R^0$ and $R^4$ have the same meanings as defined above.

Process 9

A compound represented by the above general formula (XI) can be obtained by dissolving a compound represented by the above general formula (IX) in an inert solvent, allowing the compound to react with lithium 2,6,6,6-tetramethylpyridineamide, usually at −100° C. to −50° C. and usually for 10 minutes to 2 hours, and allowing the resulting compound to react with a compound represented by the above general formula (X) usually at −100° C. to room temperature. As the inert solvent used, tetrahydrofuran, diethyl ether, 1,2-dimethoxyethane, a mixed solvent thereof or the like can be illustrated. The reaction time of the condensation reaction is usually from 30 minutes to 6 hours, varying based on a used starting material, solvent and reaction temperature.

Process 10

A compound represented by the above general formula (Va) can be prepared by allowing a compound represented by the above general formula (XI) to react with benzyl alcohol in the presence of tris[2-(2-methoxyethoxy)ethyl] amine using a base such as potassium hydroxide, sodium hydroxide, potassium carbonate, sodium carbonate, sodium hydrogen carbonate or the like, in a solvent such as toluene, benzene, or the like. The reaction temperature is usually from room temperature to reflux temperature, and the reaction time is usually from 1 hour to 1 day, varying based on a used starting material, solvent and reaction temperature.

Process 11

A compound represented by the above general formula (IIIb) can be prepared by subjecting a compound represented by the above general formula (Va) optionally to removal of the protective group in the usual way and then to hydrogenation in the presence or absence of an acid such as hydrochloric acid using a palladium catalyst such as palladium-carbon powder in an inert solvent under a hydrogen atmosphere. As the solvent used in the hydrogenation, for example, methanol, ethanol, tetrahydrofuran, ethyl acetate, acetic acid, isopropanol, a mixed solvent thereof or the like can be illustrated. The reaction temperature is usually from room temperature to reflux temperature, and the reaction time is usually from 1 hour to 1 day, varying based on a used starting material, solvent and reaction temperature.

Of compounds represented by the above general formula (III) as a starting material in the above production method (Scheme 1), a compound represented by the following general formula (IIIc) can be also prepared, for example, according to the reaction described in the following Scheme 5:

Scheme 5

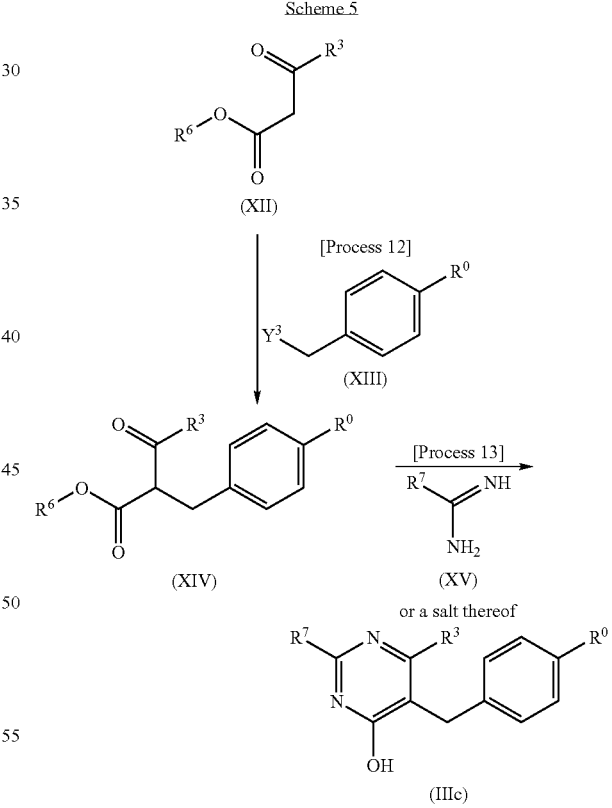

wherein $R^6$ represents a lower alkyl group; $R^7$ represents a lower alkyl group, a cyclic lower alkyl group, a lower alkoxy group, an amino group which may have a protective group, a (lower acyl)amino group, a mono(lower alkyl) amino group which may have a protective group or a di (lower alkyl) amino group; $Y^3$ represents a leaving group such as a halogen atom, a mesyloxy group a tosyloxy group or the like; and $R^0$ and $R^3$ have the same meanings as defined above.

Process 12

A compound represented by the above general formula (XIV) can be prepared by subjecting a compound represented by the above general formula (XII) to 1) condensation with a benzyl derivative represented by the above general formula (XIII) in the presence of a base such as sodium hydride, potassium tert-butoxide or the like in a solvent such as 1,2-dimethoxyethane, tetrahydrofuran, N,N-dimethylformamide, N,N-dimethyl-acetoamide or the like, or to 2) condensation with a benzyl derivative represented by the above general formula (XIII) in the presence or absence of lithium bromide or lithium chloride using a base such as diisopropylethylamine, triethylamine, 1,8-diazabicyclo-[5,4,0]-7-undecene or the like in a solvent such as tetrahydrofuran, diethylether, N,N-dimethylformamide, N,N-dimethylacetoamine or the like. At the reaction 1), the reaction temperature is usually from room temperature to reflux temperature, and the reaction time is usually from 1 hour to 1 day, varying based on a used starting material, solvent and reaction temperature. In addition, at the reaction 2), the reaction temperature is usually from room temperature to reflux temperature, and the reaction time is usually from 1 hour to 1 day, varying based on a used starting material, solvent and reaction temperature.

Process 13

A compound represented by the above general formula (IIIc) can be prepared by allowing a compound represented by the above general formula (XIV) to react with a compound represented by the above general formula (XV) or a salt thereof in the presence or absence of a base such as sodium methoxide, sodium ethoxide or the like in an alcoholic solvent. As the alcoholic solvent used in the reaction, for example, methanol, ethanol, propanol, a mixed solvent thereof or the like can be illustrated. The reaction temperature is usually from room temperature to ref lux temperature, and the reaction time is usually from 2 hours to 2 days, varying based on a used starting material, solvent and reaction temperature.

Of compounds represented by the above general formula (III) as a starting material in the above production method (Scheme 1), a compound represented by the following general formula (IIId) can be also prepared, for example, according to the reaction described in the following Scheme 6:

Scheme 6

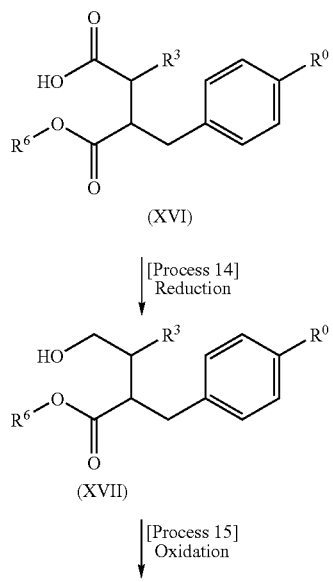

(XVI)

[Process 14]
Reduction (XVII)

[Process 15]
Oxidation

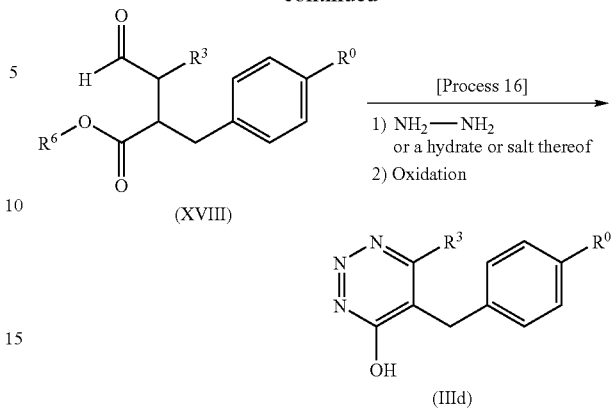

(XVIII)

[Process 16]
1) $NH_2$—$NH_2$
   or a hydrate or salt thereof
2) Oxidation (IIId)

wherein $R^0$, $R^3$ and $R^6$ have the same meanings as defined above.

Process 14

A compound represented by the above general formula (XVII) can be obtained by reducing a compound represented by the above general formula (XVI) using a reducing agent such as borane-tetrahydrofuran complex, borane-dimethylsulfide complex or the like in an inert solvent. As the inert solvent used in the reduction, tetrahydrofuran, diethyl ether, a mixed solvent thereof or the like can be illustrated. The reaction temperature is usually from 0° C. to reflux temperature, and the reaction time is usually from 1 hour to 1 day, varying based on a used starting material, solvent and reaction temperature. In addition, a starting material represented by the above general formula (XVI) can be commercially available or prepared by reaction according to a manner described in literature or an analogous method thereof, for example, J. Org. Chem., Vol. 37, pp. 555-559 (1972), SYNLETT, pp. 137-138 (1993).

Process 15

A compound represented by the above general formula (XVIII) can be prepared by subjecting a compound represented by the above general formula (XVII) to oxidation using a Dess-Martin reagent. As the solvent used in the oxidation, for example, dichloromethane, chloroform, a mixed solvent thereof or the like can be illustrated. The reaction temperature is usually from 0° C. to reflux temperature, and the reaction time is usually from 30 minutes to 1 day, varying based on a used starting material, Process 16

A compound represented by the above general formula (IIId) can be prepared by subjecting a compound represented by the above general formula (XVIII) to cyclization by reaction with hydrazine or a hydrate thereof or a salt thereof in a solvent such as methanol, ethanol, toluene, benzene or a mixed solvent thereof, and then to oxidation using selenium dioxide or the like in an alcoholic solvent such as methanol, ethanol or the like. At the cyclization reaction, the reaction temperature is usually from room temperature to reflux temperature, and the reaction time is usually from 30 minutes to 1 day, varying based on a used starting material, solvent and reaction temperature. At the oxidation reaction, the reaction temperature is usually from room temperature to reflux temperature, and the reaction time is usually from 30 minutes to 2 days, varying based on a used starting material, solvent and reaction temperature.

A compound represented by the above general formula (V) as a starting material in the above production method (Scheme 2) can be prepared, for example, according to the reaction described in the following Scheme 7:

Scheme 7

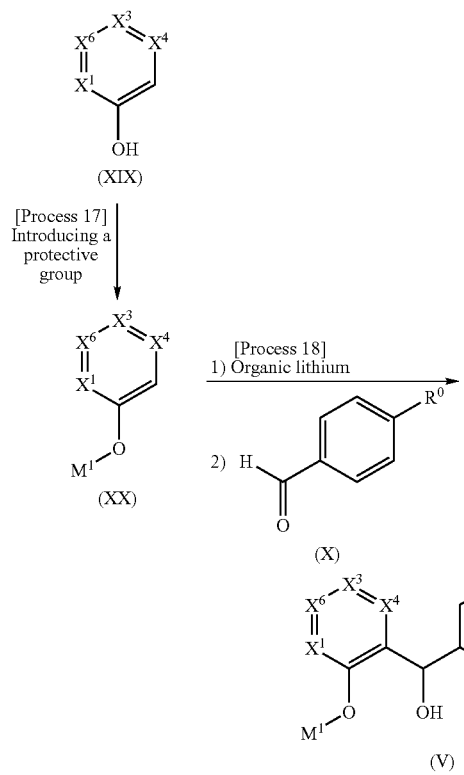

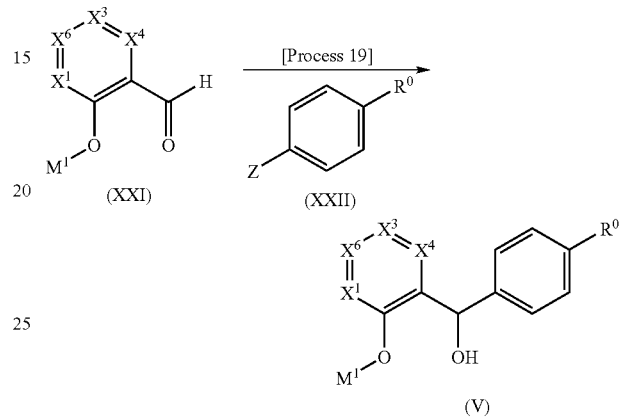

wherein $X^1$, $X^3$, $X^4$, $X^6$, $R^0$ and $M^1$ have the same meanings as defined above.

Process 17

A compound represented by the above general formula (XX) can be prepared by introducing a protective group $M^1$ into the hydroxy group of a compound represented by the above general formula (XIX) in the usual way.

Process 18

A compound represented by the above general formula (V) can be prepared by dissolving a compound represented by the above general formula (XX) in an inert solvent, allowing the compound to react with an organic lithium such as tert-butyllithium, n-butyllithium or the like usually at −100° C. to 0° C. usually for 10 minutes to 2 hours, then allowing the resulting compound to react with a compound represented by the above general formula (X) added to the reaction mixture, at −100° C. to room temperature. As the inert solvent used in the present reaction, tetrahydrofuran, diethyl ether, 1,2-dimethoxyethane, a mixed solvent thereof or the like can be illustrated. The reaction time at the condensation reaction is usually from 30 minutes to 6 hours, varying based on a used starting material, solvent and reaction temperature.

A compound represented by the above general formula (V) as a starting material in the above production method (Scheme 2) can be also prepared, for example, according to the reaction described in the following Scheme 8:

Scheme 8 wherein Z represents MgBr, MgCl, MgI or a lithium atom; $X^1$, $X^3$, $X^4$, $X^6$, $R_0$ and $M^1$ have the same meanings as defined above.

Process 19

A compound represented by the above general formula (V) can be prepared by subjecting a compound represented by the above general formula (XXI) to condensation with a compound represented by the above general formula (XXII) in an inert solvent. As the solvent used in the condensation reaction, for example, tetrahydrofuran, diethyl ether, 1,2-dimethoxyethane, a mixed solvent thereof or the like can be illustrated. The reaction temperature is usually from −100° C. to room temperature, and the reaction time is usually from 30 minutes to 6 hours, varying based on a used starting material, solvent and reaction temperature.

A compound represented by the above general formula (XXI) as a starting material in the above production method (Scheme 8) can be prepared, for example, according to the reaction described in the following Scheme 9:

Scheme 9

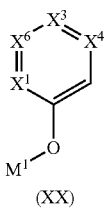

[Process 20]
Formylation

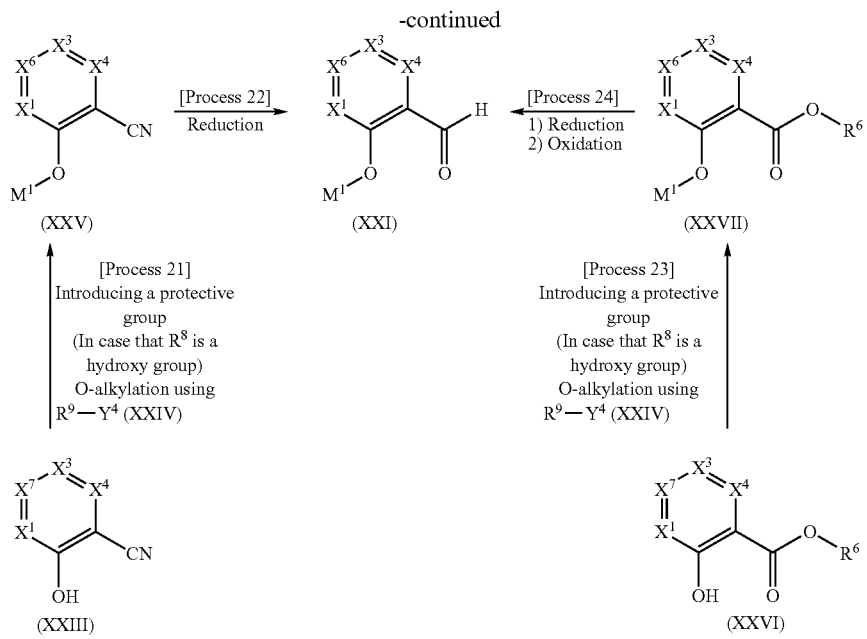

wherein $X^7$ represents N or $CR^8$; $R^8$ represents a hydrogen atom, a halogen atom, a hydroxy group, a lower alkyl group, a cyclic lower alkyl group or a lower alkoxy group; $R^9$ represents a lower alkyl group; $Y^4$ represents a leaving group such as a halogen atom, a mesyloxy group, a tosyloxy group or the like; and $X^1$, $X^3$, $X^4$, $X^6$, $R^6$ and $M^1$ have the same meanings as defined above, and with the proviso that one or two of $X^1$, $X^3$, $X^4$ and $X^7$ are N in a compound (XXIII) and a compound (XXVI).

Process 20

A compound represented by the above general formula (XXI) can be prepared by dissolving a compound represented by the above general formula (XX) in an inert solvent, allowing the compound to react with an organic lithium such as tert-butyllithium, n-butyllithium or the like usually at −100° C. to 0° C. usually for 10 minutes to 2 hours, then adding N,N-dimethylformamide, and allowing the mixture to react usually for 30 minutes to 1 day usually at −100° C. to room temperature, and treating the reaction mixture by an aqueous acidic solution. As the inert solvent used, for example, tetrahydrofuran, diethyl ether, 1,2-dimethoxyethane, a mixed solvent thereof or the like can be illustrated, and as an aqueous acidic solution, for example, an aqueous solution of acetic acid, hydrochloric acid, succinic acid, oxalic acid or the like can be illustrated. The treatment time in the aqueous acidic solution is usually from 5 minutes to 30 minutes, varying based on a used acidic solvent and reaction temperature.

Process 21

A compound represented by the above general formula (XXV) can be prepared by introducing a protective group $M^1$ into the hydroxy group of a compound represented by the above general formula (XXIII) in the usual way. In addition, optionally in case that $R^8$ is a hydroxy group, a corresponding compound can be derived by O-alkylation using a compound represented by the above general formula (XXIV) in the usual way.

Process 22

A compound represented by the above general formula (XXI) can be obtained by subjecting a compound represented by the above general formula (XXV) using a reducing agent such as diusobutylaluminum hydride or the like in an inert solvent. As the solvent used in the reaction, for example, tetrahydrofuran, dichloromethane, a mixed solvent thereof or the like can be illustrated. The reaction temperature is usually from −100° C. to room temperature, and the reaction time is usually from 1 hour to 6 days, varying based on a used starting material, solvent and reaction temperature.

Process 23

A compound represented by the above general formula (XXVII) can be prepared by introducing a protective group $M^1$ into the hydroxy group of a compound represented by the above general formula (XXVI) in the usual way. In addition, optionally in case that $R^8$ is a hydroxy group, a corresponding compound can be derived by O-alkylation using a compound represented by the above general formula (XXIV) in the usual way.

Process 24

A compound represented by the above general formula (XXI) can be prepared by subjecting a compound represented by the above general formula (XXVII) to 1) reduction using a reducing agent such as diisobutylaluminum hydride in an inert solvent, and then to 2) oxidation using an oxidizing agent such as a Dess-Martin reagent in an inert solvent. As the solvent used in the reduction, for example, tetrahydrofuran, dichloromethane, a mixed solvent thereof or the like can be illustrated, the reaction temperature is usually from −20° C. to reflux temperature, and the reaction time is usually from 1 hour to 1 day, varying based on a used starting material, solvent and reaction temperature. As the solvent used in the oxidation, for example, chloroform, dichloromethane or the like can be illustrated, the reaction temperature is usually from 0° C. to reflux temperature, and the reaction time is usually from 1 hour to 1 day, varying based on a used starting material, solvent and reaction temperature.

The nitrogen-containing heterocyclic derivatives represented by the above general formula (I) and the prodrugs thereof of the present invention obtained by the above production processes can be isolated and purified by conventional separation means such as fractional recrystallization, purification using chromatography, solvent extraction and solid phase extraction.

The nitrogen-containing heterocyclic derivatives represented by the above general formula (I) of the present invention and prodrugs thereof can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid, and the like, and salts with inorganic bases such as a sodium salt, a potassium salt and the like.

The nitrogen-containing heterocyclic derivatives represented by the above general formula (I) of the present invention and prodrugs thereof include their solvates with pharmaceutically acceptable solvents such as ethanol and water.

Among the nitrogen-containing heterocyclic derivatives represented by the above general formula (I) of the present invention and prodrugs thereof, there are two optical isomers, R-isomer and S-isomer, in each compound having an asymmetric carbon atom excluding the glucopyranosyloxy moiety. In the present invention,either of R-isomer or S-isomer can be employed, and a mixture of both isomers can be also employed.

The nitrogen-containing heterocyclic derivatives represented by the above general formula (I) of the present invention and prodrugs thereof show an activity of lowering blood glucose level by an excellent inhibitory activity in human SGLT2. Therefore, they are extremely useful as drugs for the prevention or treatment of a disease associated with hyperglycemia such as diabetes, diabetic complications (e.g., retinopathy, neuropathy, nephropathy, ulcer, macroangiopathy), obesity, hyperinsulinemia, glucosemetabolism disorders, hyperlipidemia, hypercholesterolemia, hypertriglyceridemia, lipid metabolism disorders, atherosclerosis, hypertension, congestive heart failure, edema, hyperuricemia, gout or the like.

Furthermore, the compounds of the present invention can be suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of same or different administration route, and administration at different dosage intervals as separated preparations in way of same or different administration route. A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above-drugs. Also, the administration dose can be decreased in comparison with administration of either drug alone, or adverse effects of coadministered drugs other than SGLT2 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, diabetic complications, obesity, hyperinsulinemia, glucose metabolism disorders, hyperlipidemia, hypercholesterolemia, hypertriglyceridemia, lipid metabolism disorders or atherosclerosis, and more preferably for diabetes, hyperinsulinemia or glucose metabolism disorders because of improving the disturbance of insulin signal transduction in peripheral tissues and enhancing glucose uptake into the tissues from the blood, leading to lowering blood glucose level.

As glucose absorption inhibitors, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorders, and more preferably for diabetes or glucose metabolism disorders because of inhibiting the gastrointestinal enzymatic digestion of carbohydrates contained in foods, and inhibiting or delaying the absorption of glucose into the body.

As biguanides, phenformin, buformin hydrochloride, metformin hydrochloride and the like are illustrated. Biguanides are used preferably for diabetes, diabetic complications, hyperinsulinemia or glucose metabolism disorders, and more preferably for diabetes, hyperinsulinemia or glucose metabolism disorders because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. Insulin secretion enhancers are used preferably for diabetes, diabetic complications or glucose metabolism disorders, and more preferably for diabetes or glucose metabolism disorders because of lowering blood glucose level by acting on pancreatic β-cells and enhancing the insulin secretion.

As insulin or insulin analogues, human insulin, animal-deprived insulin and human insulin analogues are illustrated. These agents are used preferably for diabetes, diabetic complications or glucose metabolism disorders, and more preferably for diabetes or glucose metabolism disorders.

As glucagon receptor antagonists, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, NVP-DPP728A, TSL-225, P-32/98 and the like are illustrated; as protein tyrosine phosphatase 1B inhibitors, PTP-112, OC-86839, PNU-177496 and the like are illustrated; as glycogen phosphorylase inhibitors, NN-4201, CP-368296 and the like are illustrated; as fructose-bisphosphatase inhibitors, R-132917 and the like are illustrated; as pyruvate dehydrogenase inhibitors, AZD-7545 and the like are illustrated; as hepatic gluconeogenesis inhibitors, FR-225659 and the like are illustrated; as glucagon-like peptide-1 analogues, exendin-4, CJC-1131 and the like are illustrated; as glucagon-like peptide 1 agonists; AZM-134, LY-315902 and the like are illustrated; and as amylin, amylin analogues or amylin agonists, pramlintide acetate and the like are illustrated. These drugs, glucose-6-phosphatase inhibitors, D-chiroinositol, glycogen synthase kinase-3 inhibitors, glucagon-like peptide-1 are used preferably for diabetes, diabetic complications, hyperinsulinemia or glucose metabolism disorders, and more preferably for diabetes or glucose metabolism disorders.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride and the like are illustrated. Advanced glycation endproducts formation inhibitors are preferably used for diabetic complications because of inhibiting formation of advanced glycation endproducts which are accelerated in continuous hyperglycemic condition in diabetes and declining cellular damage.

As protein kinase C inhibitors, LY-333531, midostaurin and the like are illustrated. Protein kinase C inhibitors are preferably used for diabetic complications because of inhibiting protein kinase C activity which is accelerated in continuous hyperglycemic condition in diabetes.

As γ-aminobutyric acid receptor antagonists, topiramate and the like are illustrated; as sodium channel antagonists, mexiletine hydrochloride, oxcarbazepine and the like are illustrated; as transcrit factor NF-κB inhibitors, dexlipotam and the like are illustrated; as lipid peroxidase inhibitors, tirilazad mesylate and the like are illustrated; as N-acetylated-α-linked-acid-dipeptidase inhibitors, GPI-5693 and the like are illustrated; and as carnitine derivatives, carnitine, levacecarnine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for hyperlipidemia, hypercholesterolemia, hypertriglyceridemia, lipid metabolism disorders or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for hyperinsulinemia, hyperlipidemia, hypercholesterolemia, hypertriglyceridemia, lipid metabolism disorders or atherosclerosis, and more preferably for hyperlipidemia, hypertriglyceridemia or atherosclerosis because of activating hepatic lipoprotein lipase and enhancing fatty acid oxidation, leading to lowering blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 and the like are illustrated. $\beta_3$-Adrenoceptor agonists are used preferably for obesity, hyperinsulinemia, hyperlipidemia, hypercholesterolemia, hypertriglyceridemia or lipid metabolism disorders, and more preferably for obesity or hyperinsulinemia because of stimulating $\beta_3$-adrenoceptor in adipose tissue and enhancing the fatty acid oxidation, leading to induction of energy expenditure.

As acyl-coenzyme A: cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A: cholesterol acyltransferase inhibitors are used preferably for hyperlipidemia, hyper-cholesterolemia, hypertriglyceridemia or lipid metabolism disorders, and more preferably for hyperlipidemia or hyper-cholesterolemia because of lowering blood cholesterol level by inhibiting acyl-coenzyme A: cholesterol acyltransferase.

As thyroid hormone receptor agonists, sodium liothyronine, sodium levothyroxine, KB-2611 and the like are illustrated; as cholesterol absorption inhibitors, ezetimibe, SCH-48461 and the like are illustrated; as lipase inhibitors, or list at, ATL-962, AZM-131, RED-103004 and the like are illustrated; as carnitine palmitoyl transferase inhibitors, etomoxir and the like are illustrated; as squalene synthase inhibitors, SDZ-268-198, BMS-188494, A-87049, RPR-101821, ZD-9720, RPR-107393, ER-27856 and the like are illustrated; as nicotinic acid derivatives, nicotinic acid, nicotinamide, nicomol, niceritrol, acipimox, nicorandil and the like are illustrated; as bile acid sequestrants, colestyramine, colestilan, colesevelam hydrochloride, GT-102-279 and the like are illustrated; as sodium/bile acid cotransporter inhibitors, 264W94, S-8921, SD-5613 and the like are illustrated; and as cholesterol ester transfer protein inhibitors, PNU-107368E, SC-795, JTT-705, CP-529414 and the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorders.

As appetite suppressants, monoamine reuptake inhibitors, serotonin reuptake inhibitors, serotonin releasing stimulants, serotonin agonists (especially 5HT$_{2C}$-agonists), noradrenalin reuptake inhibitors, noradrenalin releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, H$_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotropin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone receptor antagonists, agouti-related protein inhibitors and orexin receptor antagonists are illustrated. Concretely, as monoamine reuptake inhibitors, mazindol and the like are illustrated; as serotonin reuptake inhibitors, dexfenfluramine hydrochloride, fenfluramine, sibutramine hydrochloride, fluvoxamine maleate, sertraline hydrochloride and the like are illustrated; as serotonin agonists, inotriptan, (+)-norfenfluramine and the like are illustrated; as noradrenaline reuptake inhibitors, bupropion, GW-320659 and the like are illustrated; as noradrenaline releasing stimulants, rolipram, YM-992 and the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonists, ER-230, doprexin, bromocriptine mesylate and the like are illustrated; as cannabinoid receptor antagonists, rimonabant and the like are illustrated; as $\gamma$-aminobutyric acid receptor antagonists, topiramate and the like are illustrated; as H$_3$-histamine antagonists, GT-2394 and the like are illustrated; as leptin, leptin analogues or leptin receptor agonists, LY-355101 and the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 and the like are illustrated; and as neuropeptide Y antagonists, SR-120819-A, PD-160170, NGD-95-1, BIBP-3226, 1229-U-91, CGP-71683, BIBO-3304, CP-671906-01, J-115814 and the like are illustrated. Appetite suppressants are used preferably for diabetes, diabetic complications, obesity, glucose metabolism disorders, hyperlipidemia, hyper-cholesterolemia, hypertriglyceridemia, lipid metabolism disorders, atherosclerosis, hypertension, congestive heart failure, edema, hyperuricemia or gout, and more preferably for obesity-because of stimulating or inhibiting the activities of intracerebral monoamines or bioactive peptides in central appetite regulatory system and suppressing the appetite, leading to reduction-of energy intake.

As angiotensin-converting enzyme inhibitors, captopril, enalaprimaleate, alacepril, delaprilhydrochloride, ramipril, lisinopril, imidaprilhydrochloride, benazeprilhydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril and the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are preferably used for diabetic complications or hypertension.

As endothelin-converting enzyme inhibitors, CGS-31447, CGS-35066, SM-19712 and the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, indapamide, todralazine hydrochloride, hydralazine hydrochloride, cadralazine, budralazine and the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol nialonate, nipradilol, penbutolol sulfate, acebutolol hydrochloride, tilisolol hydrochloride, nadolol, urapidil, indoramin and the like are illustrated; as centrally acting antihypertensive agents, reserpine and the like are illustrated; and as α₂-adrenoceptor agonists, clonidine hydrochloride, methyldopa, CHF-1035, guanabenz acetate, guanfacine hydrochloride, moxonidine, lofexidine, talipexole hydrochloride and the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are preferably used for atherosclerosis or congestive heart failure.

As uric acid synthesis inhibitors, allopurinol, oxypurinol and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are preferably used for hyperuricemia or gout.

In case of use in combination with drugs other than SGLT2 inhibitors, for example, for diabetes, the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer and insulin or an insulin analogue is most preferable. Similarly, for diabetic complications, the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, for obesity, the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting with and dissolving in an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms. In case of the use of the compound of the present invention in combination with the drugs other than SGLT2 inhibitors, they can be prepared by formulating each active ingredient together or individually.

When the pharmaceutical compositions of the present invention are employed in the practical treatment, the dosage of a nitrogen-containing heterocyclic derivative represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT2 inhibitors, the dosage of the compound of the present invention can be decreased depending on the dosage of the drugs other than SGLT2 inhibitors.

EXAMPLES

The present invention is further illustrated in more detail by way of the following Reference Examples, Examples and Test Examples. However, the present invention is not limited thereto.

Reference Example 1

6-(N-Acetylamino)-3-(4-ethylbenzyl)-1H-pyridin-2-one

To a solution of tert-butyllithium (1.5 mol/L solution in hexane, 55 mL) in tetrahydrofuran (150 mL) was added 2-chloro-6-methoxypyridine (8.9 mL) at −78° C., and the mixture was stirred for 1 hour. After N,N-dimethylformamide (7.6 mL) was added to the reaction mixture, the resulting mixture was stirred for additionally 1.5 hours. To the reaction mixture was added acetic acid (8.6 mL), and the temperature was raised to room temperature. After saturated aqueous sodium bicarbonate solution was added to the resulting reaction mixture, the mixture was extracted with diethyl ether. The organic layer was washed with brine and dried over anhydrous sodium sulfate. The solvent was removed under reduced pressure, and the residue was purified by column chromatography on silica gel (eluent: hexane/ethyl acetate=15/1-3/1) to give 6-chloro-3-formyl-2-methoxypyridine (11 g). To a solution of 4-ethylbromobenzene (1.3 g) in tetrahydrofuran (14 mL) was added tert-buthyllithium (1.5 mol/L solution in hexane, 5.1 mL) at −78° C. under an argon atmosphere, and the mixture was stirred for 30 minutes. A solution of 6-chloro-3-formyl-2-methoxy-pyridine (1.0 g) in tetrahydrofuran (19 mL) was added to the reaction mixture, and the mixture was stirred at 0° C. for 30 minutes. To the reaction mixture was added saturated aqueous ammonium chloride solution, and mixture was extracted with diethyl ether. After the organic layer was dried over anhydrous sodium sulfate, the solvent was removed under reduced pressure, and the residue was purified by column chromatography on silica gel (eluent: hexane/ethyl acetate=7/1) to give 6-chloro-2-methoxypyridin-3-yl 4-ethylphenyl methanol (1.4 g). To a solution of the obtained 6-chloro-2-methoxypyridin-3-yl 4-ethylphenyl methanol (0.56 g) in dichloromethane (10 mL) was added a Dess-Martin reagent (1,1,1-triacetoxy-1,1-dihydro-1,2-benziodoxol-3-(1H)-on) (1.0 g), and the mixture was stirred at room temperature for 20 minutes. Saturated aqueous sodium bicarbonate solution (9 mL) and 10% aqueous sodium thiosulfate solution (9 mL) were added to the reaction mixture, and the mixture was extracted with diethyl ether. The organic layer was dried over anhydrous sodium sulfate, and the solvent was removed under reduced pressure. The residue was purified by column chromatography on silica gel (eluent: hexane/ethyl acetate=7/1) to give 6-chloro-2-methoxypyridin-3-yl 4-ethylphenyl ketone (0.44 g). The obtained 6-chloro-2-methoxypyridin-3-yl 4-ethylphenylketone (0.26 g), benzylamine (5 mL) and potassium carbonate (0.21 g) were stirred for 10 hours at 110° C. To the reaction mixture was added saturated aqueous ammonium chloride solution, and the mixture was extracted with ethyl acetate. The organic layer was washed with 1 mol/L hydrochloric acid solution and dried over anhydrous sodium sulfate. The solvent was removed under reduced pressure, and the residue was purified by column chromatography on silica gel (eluent: hexane/ethyl acetate=4/1) to give 6-benzylamino-2-methoxypyridin-3-yl 4-ethylphenyl ketone (0.24 g). To a solution of the obtained 6-benzylamino-2-methoxypyridin-3-yl 4-ethylphenyl ketone (0.24 g) in ethanol (6.9 mL) was added 10% palladium carbon powder (0.48 g), and the mixture was stirred at room temperature for 1 hour under a hydrogen atmosphere. The insoluble material was removed by filtration, and the filtrate was concentrated under reduced pressure. The residue was purified by preparative thin layer chromatography on silica gel (developing solvent: hexane/ ethyl acetate=2/1) to give 6-amino-3-(4-ethylbenzyl)-2-methoxy-pyridine (0.13 g). To the obtained 6-amino-3-(4-ethylbenzyl)-2-methoxypyridine (0.050 g) was added 30% hydrobromic acid solution in acetic acid (1 mL), and the mixture was stirred for 2 hours at 95° C. The reaction mixture was concentrated under reduced pressure, and the residue was purified by preparative thin layer chromatography on silica gel (developing solvent: dichloromethane/methanol=9/1) to give 6-(N-acetylamino)-3-(4-ethylbenzyl)-1H-pyridin-2-one (0.034 g).

$^1$H-NMR (CDCl$_3$) δ ppm: 1.19 (3H, t, J=7.7 Hz), 1.95 (3H, s), 2.58 (2H, q, J=7.7 Hz), 3.69 (2H, s), 6.33 (1H, d, J=7.4 Hz), 7.00-7.15 (5H, m), 10.41 (1H, brs)

Example 1

6-(N-Acetylamino)-2-(2,3,4,6-tetra-O-acetyl-β-D-gluco-pyranosyloxy)-3-(4-ethylbenzyl)pyridine To a solution of 6-(N-acetylamino)-3-(4-ethylbenzyl)-1H-pyridin-2-one (0.034 g) in dichloromethane (2.5 mL) were added acetobromo-α-D-glucose (0.10 g) and silver carbonate (0.17 g), and the mixture was stirred under shading for 3 hours at 50° C. The insoluble material was removed by filtration, and the filtrate was concentrated under reduced pressure. The residue was purified by preparative thin layer chromatography on silica gel (developing solvent: hexane/ethyl acetate=1/2) to give 6-(N-acetylamino)-2-(2,3,4,6-tetra-O-acetyl-β-D-gluco-pyranosyloxy)-3-(4-ethylbenzyl)pyridine (0.081 g).

$^1$H-NMR (CDCl$_3$) δ ppm: 1.20 (3H, t, J=7.6 Hz), 1.85 (3H, s), 2.03 (3H, s), 2.04 (3H, s), 2.05 (3H, s), 2.21 (3H, s), 2.59 (2H, q, J=7.6 Hz), 3.76 (1H, d, J=15.3 Hz), 3.85 (1H, d, J=15.3 Hz), 3.90-4.05 (1H, m), 4.14 (1H, dd, J=2.6, 12.3 Hz), 4.29 (1H, dd, J=4.5, 12.3 Hz), 5.15-5.25 (1H, m), 5.25-5.40 (2H, m), 6.00-6.10 (1H, m), 7.00-7.15 (4H, m), 7.41 (1H, d, J=7.9 Hz),7.61 (1H, brs), 7.75 (1H, brd, J=7.9 Hz)

Reference Example 2

6-Amino-3-(4-ethylbenzyl)-1H-pyridin-2-one

To a solution of 6-(N-acetylamino)-3-(4-ethylbenzyl)-1H-pyridin-2-one (0.19 g) in methanol (1 mL) was added 2 mol/L aqueous sodium hydroxide solution (0.35 mL), and the mixture was added for 22 hours at 80° C. The reaction mixture was concentrated under reduced pressure, and the residue was purified by column chromatography on silica gel (eluent: dichloro-methane/methanol=6/1) to give 6-amino-3-(4-ethylbenzyl)-1H-pyridin-2-one (0.013 g).

$^1$H-NMR (CDCl$_3$) δ ppm: 1.21 (3H, t, J=7.6 Hz), 2.60 (2H, q, J=7.6 Hz), 3.69 (2H, s), 4.73 (2H,brs), 5.32 (1H, d, J=7.6 Hz), 7.02 (1H, d, J=7.6 Hz), 7.05-7.15 (4H, m)

Example 2

6-Amino-2-(2,3,4,6-tetra-O-acetyl-β-D-glucopyranosyloxy)-3-(4-ethylbenzyl)pyridine The title compound was prepared in a similar manner to that described in Example 1 using 6-amino-3-(4-ethylbenzyl)-1H-pyridin-2-one instead of 6-(N-acetylamino)-3-(4-ethylbenzyl)-1H-pyridin-2-one.

$^1$H-NMR (CDCl$_3$) δ ppm: 1.20 (3H, t, J=7.6 Hz), 1.83 (3H, s), 2.02 (3H, s), 2.05 (3H, s), 2.07 (3H, s), 2.59 (2H, q, J=7.6 Hz) 3.67 (1H, d, J=15.4 Hz), 3.79 (1H, d, J=15.4 Hz), 3.85-4.00 (1H, m), 4.05-4.35 (2H, m), 5.15-5.40 (3H, m), 6.00-6.15 (2H, m), 7.00-7.20 (5H, m)

Reference Example 3

3-(4-Ethylbenzyl)-4,6-dimethyl-1H-pyridin-2-one

To a solution of 3-cyano-4,6-dimethyl-1H-pyridin-2-one (4.6 g) in dichloromethane (150 mL) were added benzyl bromide (5.6 mL) and silver carbonate (26 g), and the mixture was stirred under shading for 3 hours at 50° C. The reaction mixture was cooled to room temperature, and the insoluble material was removed by filtration. The filtrate was concentrated under reduced pressure, and the residue was purified by column chromatography on silica gel (eluent: hexane/ethyl acetate=7/1) to give 2-benzyloxy-3-cyano-4,6-dimethylpyridine (7.1 g). To diisobutylaluminum hydride (1.5 mol/L solution in toluene, 8.7 mL) was added a solution of 2-benzyloxy-3-cyano-4,6-dimethylpyridine (2.4 g) in tetrahydrofuran (4.3 mL) at 0° C., and the mixture was stirred for 4 hours at 0° C. The reaction mixture was poured into 1 mol/L hydrochloric acid solution (40 mL), and the mixture was extracted with diethyl ether. The organic layer was dried over anhydrous sodium sulfate, and the solvent was removed under reduced pressure. The residue was purified by column chromatography on silica gel (eluent: hexane/ethyl acetate=50/1-20/1-10/1) to give 2-benzyloxy-3-formyl-4,6-dimethylpyridine (0.90 g). To a solution of 4-ethylbromobenzene (0.044 g) in tetrahydrofuran (1.2 mL) was added tert-butyllithium (1.5 mol/L solution in hexane, 0.17 mL) at −78° C. under an argon atmosphere, and the mixture was stirred for 30 minutes. A solution of 2-benzyloxy-3-formyl-4,6-dimethylpyridine (0.048 g) in tetrahydrofuran (1.3 mL) was added to the reaction mixture, and the mixture was stirred for 30 minutes for 0° C. To the reaction mixture was added saturated aqueous ammonium chloride solution, and the mixture was extracted with diethylether. The organic layer was dried over anhydrous sodium sulfate and concentrated under reduced pressure. The residue was purified by preparative thin layer chromatography on silica gel (developing solvent: hexane/ethyl acetate=5/1) to give 2-benzyloxy-4,6-dimethylpyridin-3-yl-4-ethylphenylmethanol (0.066 g). To a solution of the obtained 2-benzyloxy-4,6-dimethylpyridin-3-yl-4-ethylphenylmethanol (0.061 g) in ethanol (3.5 mL) was added 10% palladium carbon powder (0.037 g), and the mixture was stirred for 12 hours at room temperature under a hydrogen atmosphere. The insoluble material was removed by filtration, and the filtrate was concentrated under reduced pressure. The residue was purified by preparative thin layer chromatography on silica gel (developing solvent: dichloro-methane/methanol=10/1) to give 3-(4-ethylbenzyl)-4,6-dimethyl-1H-pyridin-2-one (0.039 g).

$^1$H-NMR (CDCl$_3$) δ ppm: 1.19 (3H, t, J=7.6 Hz), 2.14 (3H, s), 2.20 (3H, s), 2.59 (2H, q, J=7.6 Hz), 3.90 (2H, s), 5.85 (1H, s), 7.00-7.10 (2H, m), 7.15-7.25 (2H, m), 12.71 (1H, brs)

Example 3

2-(2,3,4,6-Tetra-O-acetyl-β-D-glucopyranosyloxy)-3-(4-ethylbenzyl)-4,6-dimethylpyridine The title compound was prepared in a similar manner to that described in Example 1 using 3-(4-ethylbenzyl)-4,6-dimethyl-1H-pyridin-2-one instead of 6-(N-acetylamino)-3-(4-ethylbenzyl)-1H-pyridin-2-one.

¹H-NMR (CDCl₃) δ ppm: 1.17 (3H, t, J=7.6 Hz), 1.70 (3H, s), 2.00 (3H, s), 2.04 (3H, s), 2.05 (3H, s), 2.18 (3H, s), 2.37 (3H, s), 2.56 (2H, q, J=7.6 Hz), 3.81 (1H, d, J=15.3 Hz), 3.90-4.05 (2H, m), 4.14 (1H, dd, J=2.5, 12.2 Hz), 4.26 (1H, dd, J=4.8, 12.2 Hz), 5.10-5.40 (3H, m), 6.18 (1H, d, J=8.2 Hz), 6.68 (1H, s), 6.90-7.10 (4H, m)

Reference Example 4

3-(4-Methoxybenzyl)-4,6-dimethyl-1H-pyridin-2-one

A Grignard reagent (0.5 mol/L solution in tetrahydrofuran) was prepared in the usual way from 4-bromoanisole, magnesium, a catalytic amount of iodine and tetrahydrofuran. The obtained Grignard reagent (0.41 mL) was added to a solution of 2-benzyloxy-3-formyl-4,6-dimethylpyridine (0.019 g) in tetrahydrofuran (0.8 mL), and the mixture was stirred for 80 minutes at room temperature. To the reaction mixture was added saturated aqueous ammonium chloride solution, and the mixture was extracted with diethyl ether. The organic layer was dried over anhydrous sodium sulfate and concentrated under reduced pressure. The residue was purified by preparative thin layer chromatography on silica gel (developing solvent: hexane/ethyl acetate=4/1) to give 2-benzyloxy-4,6-dimethylpyridin-3-yl 4-Methoxyphenyl methanol (0.014 g) To a solution of the obtained 2-benzyloxy-4,6-dimethylpyridin-3-yl 4-methoxyphenyl methanol (0.014 g) in ethanol (1 mL) was added a catalytic amount of 10% palladium carbon powder, and the mixture was stirred for 2 hours at room temperature under a hydrogen atmosphere. The insoluble material was removed by filtration, and the filtrate was concentrated under reduced pressure. The residue was purified by preparative thin layer chromatography on silica gel (developing solvent: dichloromethane/methanol=10/1) to give 3-(4-methoxybenzyl)-4,6-dimethyl-1H-pyridin-2-one (0.010 g).

¹H-NMR (CDCl₃) δ ppm: 2.14 (3H, s), 2.21 (3H, s), 3.75 (3H, s), 3.87 (2H, s), 5.85 (1H, s), 6.70-6.80 (2H, m), 7.10-7.25 (2H, m), 12.70 (1H, brs)

Example 4

2-(2,3,4,6-Tetra-O-acetyl-β-D-glucopyranosyloxy)-3-(4-methoxybenzyl)-4,6-dimethylpyridine The title compound was prepared in a similar manner to that described in Example 1 using 3-(4-methoxybenzyl)-4,6-dimethyl-1H-pyridin-2-one instead of 6-(N-acetylamino)-3-(4-ethylbenzyl)-1H-pyridin-2-one.

¹H-NMR (CDCl₃) δ ppm: 1.75 (3H, s), 2.00 (3H, s), 2.04 (3H, s), 2.05 (3H, s), 2.17 (3H, s), 2.37 (3H, s), 3.74 (3H, s), 3.79 (1H, d, J=15.3 Hz), 3.90-4.00 (2H, m), 4.14 (1H, dd, J=2.3, 12.3 Hz), 4.25 (1H, dd, J=4.8, 12.3 Hz), 5.10-5.40 (3H,m), 6.19 (1H, d, J=8.0 Hz), 6.67 (1H, s), 6.70-6.80 (2H, m), 6.90-7.00 (2H, m)

Reference Example 5

3-[4-(2-Methoxymethyloxyethyl)benzyl]-4,6-dimethyl-1H-pyridin-2-one

To a solution of 4-(2-methoxymethyloxyethyl) bromobenzene (0.60 g) in tetrahydrofuran (6 mL) was added tert-butyllithium (1.5 mol/L solution in hexane, 2.0 mL) at −78° C. under an argon atmosphere, and the mixture was stirred for 30 minutes. Then, a solution of 2-benzyloxy-3-formyl-4,6-dimethylpyridine (0.49 g) in tetrahydrofuran (5 mL) was added to the reaction mixture, and the mixture was stirred for 3 hours at 0° C. To the reaction mixture was added saturated aqueous ammonium chloride solution, and the mixture was extracted with dimethyl ether. The organic layer was dried over anhydrous sodium sulfate and concentrated under reduced pressure. The residue was purified by column chromatography on silica gel (eluent: hexane/ethyl acetate=5/1) to give 2-benzyloxy-4,6-dimethylpyridin-3-yl 4-(2-methoxymethyloxyethyl)phenyl methanol (0.74 g). To a solution of the obtained 2-benzyloxy-4,6-dimethylpyridin-3-yl 4-(2-methoxymethyloxyethyl)phenyl methanol (0.11 g) in ethanol (5.3 mL) was added 10% palladium carbon powder (0.065 g), and the mixture was stirred for 11 hours at room temperature under a hydrogen atmosphere. The insoluble material was removed by filtration, and the filtrate was concentrated under reduced pressure. The residue was purified by preparative thin layer chromatography on silica gel (developing solvent: dichloro-methane/methanol=10/1) to give 3-[4-(2-methoxymethyloxy-ethyl)benzyl]-4,6-dimethyl-1H-pyridin-2-one (0.074 g).

¹H-NMR (CDCl₃) δ ppm: 2.13 (3H, s), 2.21 (3H, s), 2.84 (2H, t, J=7.2 Hz), 3.29 (3H, s), 3.72 (2H, t, J=7.2 Hz), 3.91 (2H, s), 4.60 (2H, s), 5.85 (1H, s), 7.05-7.15 (2H, m), 7.15-7.25 (2H, m), 12.53 (1H, brs)

Example 5

2-(2,3,4,6-Tetra-O-acetyl-β-D-glucopyranosyloxy)-3-[4-(2-methoxymethyloxyethyl)benzyl]-4,6-dimethylpyridine The title compound was prepared in a similar manner to that described in Example 1 using 3-[4-(2-methoxymethyloxy-ethyl)benzyl]-4,6-dimethyl-1H-pyridin-2-one instead of 6-(N-acetylamino)-3-(4-ethylbenzyl)-1H-pyridin-2-one.

¹H-NMR (CDCl₃) δ ppm: 1.72 (3H, s), 2.00 (3H, s), 2.04 (3H, s), 2.05 (3H, s), 2.15 (3H, s), 2.37 (3H, s), 2.83 (2H, t, J=7.0 Hz), 3.28 (3H, s), 3.70 (2H, t, J=7.0 Hz), 3.81 (1H, d, J=15.6 Hz), 3.90-4.15 (2H, m), 4.14 (1H, dd, J=2.3, 12.3 Hz), 4.26 (1H, dd, J=4.7, 12.3 Hz), 4.59 (2H, s), 5.10-5.40 (3H, m), 6.18 (1H, d, J=8.0 Hz), 6.67 (1H, s), 6.90-7.10 (4H, m)

Example 6

2-(β-D-Glucopyranosyloxy)-3-[4-(2-methoxymethyloxyethyl)-benzyl]-4,6-dimethylpyridine To a solution of 2-(2,3,4,6-tetra-O-acetyl-β-D-glucopyranosyloxy)-3-[4-(2-methoxymethyloxyethyl)benzyl]-4,6-dimethylpyridine (0.13 g) in methanol (4.0 mL) was added 2 mol/L aqueous sodium hydroxide solution (0.50 mL), and the mixture was stirred for 30 minutes at room temperature. After the reaction mixture was concentrated under reduced pressure, the residue was purified by preparative thin layer chromatography on silica gel (developing solvent: dichloromethane/methanol=9/1) to give 2-(β-D-glucopyranosyloxy)-3-[4-(2-methoxy-methyloxyethyl)benzyl]-4,6-dimethylpyridine (0.086 g).

¹H-NMR (CD₃OD) δ ppm: 2.17 (3H, s), 2.36 (3H, s), 2.80 (2H, t, J=7.0 Hz), 3.23 (3H, s), 3.30-3.55 (4H, m), 3.60-3.75 (3H, m), 3.84 (1H, dd, J=2.3, 12.0 Hz), 3.95 (1H, d, J=15.2 Hz), 4.06 (1H, d, J=15.2 Hz), 4.56 (2H, s), 5.85-5.95 (1H, m), 6.73 (1H, s), 7.05-7.15 (4H, m)

Reference Example 6

6-Methoxy-3-(4-methoxybenzyl)-4-methyl-1H-pyridin-2-one

To a solution of 3-cyano-2,6-dimethoxy-4-methylpyridine (0.11 g) in tetrahydrofuran (3 mL) was added diisobutylaluminum hydride (1.5 mol/L solution in toluene, 0.53 mL) at 0° C. The temperature was raised to room temperature, and the reaction solution was stirred for 5 days. To the reaction mixture was added 1 mol/L hydrochloric acid, and the mixture was extracted with diethyl ether. The organic layer was dried over anhydrous sodium sulfate, and the solvent was removed under reduced pressure. The residue was purified by preparative thin layer chromatography on silica gel (developing solvent: hexane/ethyl acetate=9/1) to give 3-formyl-2,6-dimethoxy-4-methylpyridine (0.034 g). To a solution of 3-formyl-2,6-dimethoxy-4-methyl-pyridine (0.033 g) in tetrahydrofuran (1.2 mL) was added a Grignard reagent (0.5 mol/L solution in tetrahydrofuran, 0.72 mL) prepared from 4-bromoanisole, magnesium, a catalytic amount of iodine and tetrahydrofuran in the usual way, and the mixture was stirred for 1 hour at room temperature. To the reaction mixture was added saturated aqueous ammonium chloride solution, and the mixture was extracted with diethyl ether. The organic layer was dried over anhydrous sodium sulfate and concentrated under reduced pressure. The residue was purified by preparative thin layer chromatography on silica gel (developing solvent: hexane/ethyl acetate=5/1) to give 2,6-dimethoxy-4-methyl-pyridin-3-yl4-methoxyphenyl methanol (0.053 g). To a solution of the obtained 2,6-dimethoxy-4-methylpyridin-3-yl 4-methoxyphenyl methanol (0.053 g) in dichloromethane (1.5 mL) was added a Dess-Martin reagent (1,1,1-triacetoxy-1,1-dihydro-1,2-benziodoxol-3(1H)-one)(0.093 g), and the mixture was stirred for 45 minutes at room temperature. To the reaction mixture were added saturated aqueous sodium bicarbonate solution (1 mL) and 10% sodium thiosulfate solution (1 mL), and the mixture was extracted with diethyl ether. The organic layer was dried over anhydrous sodium sulfate, and the solvent was removed under reduced pressure. The residue was purified by preparative thin layer chromatography on silica gel (developing solvent: hexane/ethyl acetate=6/1) to give 2,6-dimethoxy-4-methyl-pyridin-3-yl methoxyphenyl ketone (0.043 g). To a solution of the obtained 2,6-dimethoxy-4-methylpyridin-3-yl methoxyphenyl ketone (0.042 g) in dichloromethane (1.5 mL) was added boron trichloride (1 mol/L solution in dichloromethane, 0.44 mL) at 0° C. The temperature was raised to room temperature, and the reaction solution was stirred for 30 hours. To the reaction mixture was added saturated sodium bicarbonate solution, and the mixture was extracted with ethyl acetate. The organic layer was dried over anhydrous sodium sulfate, and the solvent was removed under reduced pressure. The residue was purified by preparative thin layer chromatography on silica gel (developing solvent: hexane/ethyl acetate=1/2) to give 2-hydroxy-6-methoxy-4-methylpyridin-3-yl 4-methoxyphenylketone (0.023 g). To a solution of the obtained 2-hydroxy-6-methoxy-4-methyl-pyridin-3-yl 4-methoxyphenyl ketone (0.022 g) and boron tri fluoride diethyl ether complex (0.041 mL) in tetrahydrofuran (1.6 mL) was added sodium cyanoborohydride (0.011 g), and the mixture was stirred for 2 hours at 65° C. The reaction mixture was cooled to room temperature and extracted with diethyl ether. After the organic layer was washed with saturated aqueous sodium bicarbonate solution and dried over anhydrous sodium sulfate, the solvent was removed under reduced pressure. The residue was purified by preparative thin layer chromatography on silica gel (developing solvent: hexane/ethyl acetate=1/2) to give 6-methoxy-3-(4-methoxybenzyl)-4-methyl-1H-pyridin-2-one (0.008 g).

$^1$H-NMR (CDCl$_3$) δ ppm: 2.15 (3H, s), 3.76 (3H, s), 3.80 (3H, s), 3.87 (2H, s), 5.52 (1H, s), 6.70-6.80 (2H, m), 7.10-7.20 (2H, m), 10.50-11.50 (1H, br)

Example 7

2-(2,3,4,6-Tetra-O-acetyl-β-D-glucopyranosyloxy)-6-methoxy-3-(4-methoxybenzyl)-4-methylpyridine The title compound was prepared in a similar manner to that described in Example 1 using 6-methoxy-3-(4-methoxy-benzyl)-4-methyl-1H-pyridin-2-one instead of 6-(N-acetyl-amino)-3-(4-ethylbenzyl)-1H-pyridin-2-one.

$^1$H-NMR (CDCl$_3$) δ ppm: 1.75 (3H, s), 2.01 (3H, s), 2.04 (3H, s), 2.04 (3H, s), 2.17 (3H, s), 3.70-3.80 (4H, m), 3.80-3.95 (5H, m), 4.12 (1H, dd, J=2.1, 12.3 Hz), 4.25 (1H, dd, J=5.1, 12.3 Hz), 5.10-5.20 (1H, m), 5.25-5.40 (2H, m), 6.05 (1H,d, J=7.8 Hz), 6.29 (1H, s), 6.70-6.80 (2H, m), 6.90-7.00 (2H, m)

Reference Example 7

4-(4-Ethoxybenzyl)-3-hydroxypyridine

To a solution of 3-hydroxypyridine (0.95 g) in 1,2-dimethoxyethane (20 mL) were added sodium hydride (60%, 0.44 g) and [2-(chloromethyloxy)ethyl]trimethylsilane (2.1 mL), and the mixture was stirred for 13 hours at room temperature. To the reaction mixture was added water, and the mixture was extracted with diethyl ether. After the organic layer was dried over anhydrous sodium sulfate, the solvent was removed under reduced pressure. The residue was purified by column chromatography on silica gel (eluent: hexane/ethyl acetate=2/1) to give 3-{[2-(trimethylsilyl)ethyl]oxymethyloxy}-pyridine (0.89 g). To a solution of the obtained 3-{[2-(trimethylsilyl)ethyl]oxymethyloxy}pyridine (0.23 g) in tetrahydrofuran (6 mL) was added tert-butyllithium (1.51 mol/L solution in pentane, 0.86 mL) at −78° C., and the mixture was stirred for 40 minutes. To the reaction mixture was added a solution of 4-ethoxybenzaldehyde (0.18 g) in diethyl ether (6 mL), and the mixture was stirred for 36 minutes at −78° C. The temperature was raised to room temperature, and the reaction mixture was stirred for additionally 30 minutes. To the reaction mixture was added saturated aqueous ammonium chloride solution, and the mixture was extracted with diethyl ether. The organic layer was dried over anhydrous sodium sulfate, and the solvent was removed under reduced pressure. The residue was purified by column chromatography on silica gel (eluent: hexane/ethyl acetate=1/1) to give 4-ethoxyphenyl 3-{[2-(trimethylsilyl)-ethyl]oxymethyloxy}pyridin-4-yl methanol (0.28 g). To a solution of the obtained 4-ethoxyphenyl 3-{[2-(trimethyl-silyl)ethyl]oxymethyloxy}pyridin-4-yl methanol (0.27 g) in tetrahydrofuran (7 mL) and water (0.3 mL) was added p-toluenesulfonic acid monohydride (0.68 g), and the mixture was stirred for 1 hour at 50° C. After the reaction mixture was cooled to room temperature, saturated aqueous sodium bicarbonate solution (12 mL) was added to the reaction mixture. The insoluble material was removed by filtration, and the filtrate was extracted with mixed solvents of dichloromethane and methanol (10/1). After the organic layers combined were dried over anhydrous sodium sulfate, the solvent was removed under reduced pressure. The residue was purified by column chromatography on silica gel (eluent: dichloromethane/methanol=10/1) to give 4-ethoxyphenyl 3-hydroxypyridin-4-yl methanol (0.16 g). To a solution of the obtained 4-ethoxyphenyl 3-hydroxypyridin-4-yl methanol (0.13 g) in acetic acid (5.3 mL) was added 10% palladium carbon powder (0.13 g), and the mixture was stirred for 2 hours at room temperature under a hydrogen atmosphere. The insoluble material was removed by filtration, and the filtrate was concentrated under reduced pressure. To the residue was added ethyl acetate, and the resulting precipitated crystals were collected by filtration. The crystals were dried under reduced pressure to give 4-.(4-ethoxybenzyl)-3-hydroxypyridine (0.095 g).

$^1$H-NMR (CD$_3$OD) δ ppm: 1.36 (3H, t, J=7.0 Hz), 3.89 (2H, s), 3.99 (2H, q, J=7.0 Hz), 6.75-6.90 (2H, m), 7.00 (1H, d, J=4.9 Hz), 7.05-7.20 (2H, m), 7.87 (1H, d, J=4.9 Hz), 7.99 (1H, s)

Example 8

3-(2,3,4,6-Tetra-O-acetyl-β-D-glucopyranosyloxy)-4-(4-ethoxybenzyl)pyridine

The title compound was prepared in a similar manner to that described in Example 1 using 4-(4-ethoxybenzyl)-3-hydroxy-pyridine instead of 6-(N-acetylamino)-3-(4-ethylbenzyl)-1H-pyridin-2-one.

$^1$H-NMR (CDCl$_3$) δ ppm: 1.40 (3H, t, J=7.0 Hz), 1.96 (3H, s), 2.04 (3H, s), 2.06 (3H, s), 2.09 (3H, s), 3.80-3.95 (3H, m), 4.00 (2H, q, J=7.0 Hz), 4.17 (1H, dd, J=2.3, 12.4 Hz), 4.30 (1H, dd, J=5.7, 12.4 Hz), 5.10-5.25 (2H, m), 5.25-5.40 (2H, m), 6.75-6.85 (2H, m), 6.95 (1H, d, J=4.7 Hz), 7.00-7.10 (2H, m), 8.22 (1H, d, J=4.7 Hz), 8.36 (1H, s)

Reference Example 8

3-(4-Methoxybenzyl)-1H-pyridin-2-one

To a solution of mesityl bromide (0.77 g) in tetrahydrofuran (2.6 mL) was added tert-butyllithium (1.48 mol/L solution in pentane, 5.3 mL) at −78° C. under an argon atmosphere, and the mixture was stirred for 1 hour. To the reaction mixture was added a solution of 2-methoxypyridine (0.33 g) in tetrahydofuran (3 mL). The temperature was raised to 0° C., and the mixture was stirred for 1 hour. The temperature was raised to room temperature, and the reaction mixture was stirred for additionally 1 hour. To the reaction mixture was added a solution of 4-methoxybenzaldehyde (0.57 g) in tetrahydrofuran (4.2 mL), and the mixture was stirred for 1 hour. To the reaction mixture was added saturated aqueous ammonium chloride solution, and the mixture was extracted with diethyl ether. The organic layer was washed with water and brine, and dried over anhydrous sodium sulfate. The solvent was removed under reduced pressure, and the residue was purified by column chromatography on silica gel (eluent: hexane/ethyl acetate=3/1-2/1) to give 4-methoxyphenyl 2-methoxypyridin-3-yl methanol (0.43 g). To a solution of the obtained 4-methoxyphenyl 2-methoxypyridin-3-yl methanol (0.41 g) in acetic acid (2.1 mL) was added 10% palladium carbon powder (0.21 g), and the mixture was stirred for 10 hours at room temperature under a hydrogen atmosphere. The insoluble material was removed by filtration, and the filtrate was concentrated under reduced pressure. The residue was purified by column chromatography on silica gel (eluent: hexane/ethyl acetate=5/1-4/1) to give 2-methoxy-3-(4-methoxybenzyl)pyridine (0.29 g). To a solution of the obtained 2-methoxy-3-(4-methoxybenzyl)pyridine (0.023 g) in dichloromethane (0.5 mL) was added boron trichloride (1 mol/L solution in dichloromethane, 0.06 mL) at 0° C. The temperature was raised to room temperature, and the mixture was stirred for 1 hour. After boron trichloride (1 mol/L solution in dichloromethane, 0.06 mL) was added to the reaction mixture, the mixture was stirred for additionally 15 hours. To the reaction mixture was added water, and the mixture was extracted with a mixture of dichloromethane and ethanol (10/1). The organic layer was dried over anhydrous sodium sulfate, and the solvent was removed under reduced pressure. The residue was purified by preparative thin layer chromatography on silica gel (developing solvent: dichloromethane/methanol=8/1) to give 3-(4-methoxy-benzyl)-1H-pyridin-2-one (0.0017 g).

$^1$H-NMR (CDCl$_3$) δ ppm: 3.80 (3H, s), 3.83 (2H, s), 6.10-6.25 (1H, m), 6.89-6.95 (2H, m), 7.00-7.35 (4H, m), 12.30 (1H, brs)

Example 9

2-(2,3,4,6-Tetra-O-acetyl-β-D-glucopyranosyloxy)-3-(4-methoxybenzyl)pyridine

The title compound was prepared in a similar manner to that described in Example 1 using 3-(4-methoxybenzyl)-1H-pyridin-2-one instead of 6-(N-acetylamino)-3-(4-ethyl-benzyl)-1H-pyridin-2-one.

$^1$H-NMR (CDCl$_3$) δ ppm: 1.88 (3H, s), 2.03 (3H, s), 2.05 (3H, s), 2.06 (3H, s), 3.78 (3H, s), 3.75-3.90 (2H, m), 3.90-4.00 (1H, m), 4.12 (1H, dd, J=2.3, 12.4 Hz), 4.31 (1H, dd, J=4.5, 12.4 Hz), 5.15-5.45 (3H, m), 6.15-6.25 (1H, m), 6.75-6.85(2H, m), 6.91 (1H, dd, J=4.9, 7.3 Hz), 7.00-7.15 (2H, m), 7.34 (1H, dd, J=1.9, 7.3 Hz), 8.00 (1H, dd, J=1.9, 4.9 Hz)

Reference Example 9

5-(4-Methoxybenzyl)-2,6-dimethyl-3H-pyrimidin-4-one

A suspension of methyl acetoacetate (3.2 mL) 4-methoxybenzyl chloride (4.1 mL), lithium bromide (2.6 g) and diisopropylethylamine (5.2 mL) in tetrahydrofuran (60 mL) was heated under reflux for 15 hours. After the reaction mixture was cooled to room temperature, saturated aqueous ammonium chloride solution was added to the reaction mixture, and the mixture was extracted with diethyl ether. The organic layer was washed with water, dried over anhydrous magnesium sulfate and concentrated under reduced pressure to give methyl 2-(4-methoxybenzyl)acetoacetate. To a suspension of acetoamidine hydrochloride (2.0 g) in methanol (60 mL) was added sodium methoxide (28% solution in methanol, 2.6 mL), and the mixture was stirred for 5 minutes at room temperature. To the reaction mixture was added a solution of methyl 2-(4-methoxy-benzyl)acetoacetate in methanol (6 mL), and the mixture was stirred for 48 hours at room temperature. The reaction mixture was poured into water, and the mixture was extracted with ethyl acetate. The organic layer was dried over anhydrous magnesium sulfate, and the solvent was removed under reduced pressure. To the residue was added ethyl acetate, and the resulting precipitated crystals were collected by filtration and dried to give 5-(4-methoxybenzyl)-2,6-dimethyl-3H-pyrimidin-4-one (0.54 g).

$^1$H-NMR (DMSO-d$_6$) δ ppm: 2.14 (3H, s), 2.21 (3H, s), 3.67 (2H, s), 3.69 (3H, s), 6.75-6.85 (2H, m), 7.05-7.15 (2H, m), 12.29 (1H, brs)

Example 10

4-(2,3,4,6-Tetra-O-acetyl-β-D-glucopyranosyloxy)-5-(4-methoxybenzyl)-2,6-dimethylpyrimidine To a solution of 5-(4-methoxybenzyl)-2,6-dimethyl-3H-pyrimidin-4-one (0.30 g) in acetonitrile (6 mL) were added acetobromo-α-D-glucose (0.76 g) and potassium carbonate (0.27 g), and the mixture was stirred for 17 hours at 60° C. The insoluble material was removed by filtration, and the filtrate was concentrated under reduced pressure. The residue was purified by column chromatography on aminopropyl silica gel (eluent: hexane/ethyl acetate=1/1) and on silica gel (eluent: hexane/ethyl acetate=1/1-1/2) to give 4-(2,3,4,6-tetra-O-acetyl-β-D-glucopyranosyloxy)-5-(4-methoxybenzyl)-2,6-dimethylpyrimidine (0.24 g).
$^1$H-NMR (CDCl$_3$) δ ppm: 1.78 (3H, s), 2.01 (3H, s), 2.05 (3H, s), 2.06 (3H, s), 2.41 (3H, s), 2.56 (3H, s), 3.76 (3H, s), 3.79 (1H, d, J=15.6 Hz), 3.85-4.00 (2H, m), 4.15 (1H, dd, J=2.2, 12.4 Hz), 4.26 (1H, dd, J=4.8, 12.4 Hz), 5.10-5.40 (3H,m), 6.20 (1H, d, J=8.1 Hz), 6.70-6.80 (2H, m), 6.95-7.05 (2H, m)

Reference Example 10

4-[4-(2-Benzoyloxyethyl)benzyl]-3-hydroxypyridine

To a solution of 4-(2-benzoyloxyethyl)benzyl alcohol (1.2 g) in dichloromethane (50 mL) was added manganese dioxide (12 g), and the mixture was stirred for 23 hours at room temperature. The insoluble material was removed by filtration, and the solvent of the filtrate was removed under reduced pressure to give 4-(2-benzoyloxyethyl)benzaldehyde (0.87 g). To a solution of 3-(methoxymethyloxy)pyridine (0.20 g) in diethyl ether (20 mL) was added tert-butyllithium (1.51 mol/L solution in pentane, 1.2 mL) at −78° C., and the mixture was stirred for 30 minutes. To the reaction mixture was added a solution of 4-(2-benzoyloxyethyl)benzaldehyde (0.44 g) in diethyl ether (4 mL). The temperature was raised to room temperature, and the mixture was stirred for 1 hour. To the reaction mixture was added saturated aqueous ammonium chloride solution, and the mixture was extracted with ethyl acetate. The organic layer was washed with brine and dried over anhydrous sodium sulfate, and the solvent was removed under reduced pressure. To the residue were added hexane and ethyl acetate, and the resulting crystals were collected by filtration and dried under reduced pressure to give 4-(2-benzoyloxyethyl)phenyl-3-(methoxymethyloxy)pyridin-4-yl-methanol (0.30 g). To a solution of the obtained 4-(2-benzoyloxyethyl)phenyl-3-(methoxymethyloxy)pyridin-4-yl-methanol (0.28 g) in ethanol (4.8 mL) was added concentrated hydrochloric acid (0.6 mL), and the mixture was heated under reflux for 10 minutes. The solvent of the reaction mixture was removed under reduced pressure, and ethyl acetate was added to the residue. The resulting precipitated crystals were collected by filtration and dried to give4-(2-benzoyloxyethyl)-phenyl-3-hydroxypyridin-4-ylmethanol hydrochloride (0.28 g). To a solution of the obtained 4-(2-benzoyloxyethyl)phenyl-3-hydroxypyridin-4-ylmethanol hydrochloride (0.27 g) in ethanol (6.9 mL) was added 10% palladium carbon powder (0.27 g), and the mixture was stirred for 3.5 hours at room temperature under a hydrogen atmosphere. The insoluble material was removed by filtration, and the solvent of the filtrate was removed under reduced pressure. To the residue were added ethyl acetate and diethyl ether, and the resulting crystals were collected by filtration. To the obtained crystals was added saturated aqueous sodium bicarbonate solution, and the mixture was extracted with ethyl acetate. After the organic layer was washed with brine and dried over anhydrous sodium sulfate, the solvent was removed under reduced pressure. To the residue was added diethyl ether, and the resulting precipitated crystals were collected by filtration and dried under reduced pressure to give 4-[4-(2-benzoyloxyethyl)benzyl]-3-hydroxypyridine (0.12. g).
$^1$H-NMR (CDCl$_3$) δ ppm: 3.06 (2H, t, J=7.0 Hz), 4.01 (2H, s), 4.52 (2H, t, J=7.0 Hz), 7.00 (1H, d, J=4.8 Hz), 7.15-7.30 (4H, m), 7.35-7.45 (2H, m), 7.50-7.60 (1H, m), 7.95-8.05 (3H, m), 8.27 (1H, s)

Example 11

3-(2,3,4,6-Tetra-O-acetyl-β-D-glucopyranosyloxy)-4-[4-(2-benzoyloxyethyl)benzyl]pyridine The title compound was prepared in a similar manner to that described in Example 1 using 4-[4-(2-benzoyloxyethyl)-benzyl]-3-hydroxypyridine instead of 6-(N-acetylamino)-3-(4-ethylbenzyl)-1H-pyridin-2-one.
$^1$H-NMR (CDCl$_3$) δ ppm: 1.93 (3H, s), 2.03 (3H, s)., 2.06 (3H, s), 2.09 (3H, s), 3.05 (2H, t, J=6.9 Hz), 3.85-3.95 (3H, m), 4.17 (1H, dd, J=2.2, 12.2 Hz), 4.30 (1H, dd, J=5.7, 12.2 Hz), 4.51 (2H, t, J=6.9 Hz), 5.10-5.25 (2H, m), 5.25-5.40 (2H, m), 6.95 (1H, d, J=4.6 Hz), 7.05-7.15 (2H, m), 7.15-7.25 (2H, m), 7.35-7.50 (2H, m), 7.50-7.60 (1H, m), 7.95-8.05 (2H, m), 8.22 (1H, d, J=4.6 Hz),8.37 (1H, s)

Reference Example 11

5-(4-Ethylthiobenzyl)-2,6-dimethyl-3H-pyrimidin-4-one

To a solution of 4-ethylthiobenzyl alcohol (3.7 g) in tetrahydrofuran (80 mL) were added triethylamine (3.0 mL) and methanesulfonyl chloride (1.7 mL) at 0° C., and the mixture was stirred for 30 minutes. After the insoluble material was removed by filtration, the filtrate was added to a suspension of sodium hydride (60%, 0.88 g) and methyl acetoacetate (2.4 mL) in 1,2-dimethoxyethane (100 mL), and the mixture was heated under reflux for 4 hours. The reaction mixture was poured into saturated aqueous sodium bicarbonate solution, and the mixture was extracted with diethyl ether. The organic layer was washed with brine and dried over anhydrous magnesium sulfate, and the solvent was removed to give methyl 2-(4-ethylthiobenzyl)-acetoacetate (6.1 g). To a suspension of acetoamidine hydrochloride (0.80 g) in methanol (15 mL) was added sodium methoxide (28% solution in methanol, 1.7 mL), and the mixture was stirred for 5 minutes at room temperature. To the reaction mixture was added a solution of methyl 2-(4-ethylthiobenzyl)-acetoacetate (1.5 g) in methanol (5 mL), and the mixture was stirred for 18 hours at room temperature. The reaction mixture was poured into water, and the mixture was extracted with ethyl acetate. The organic layer was dried over anhydrous magnesium sulfate, and the solvent was removed under reduced pressure. To the residue was added ethyl acetate, and the resulting precipitated crystals were collected by filtration and dried to give 5-(4-ethylthiobenzyl)-2,6-dimethyl-3H-pyrimidin-4-one (0.33 g).

$^1$H-NMR (DMSO-d$_6$) δ ppm: 1.19 (3H, t, J=7.3 Hz), 2.15 (3H, s), 2.22 (3H, s), 2.91 (2H, q, J=7.3 Hz), 3.71 (2H, s), 7.05-7.30 (4H, m), 12.30 (1H, brs)

Example 12

4-(2,3,4,6-Tetra-O-acetyl-β-D-glucopyranosyloxy)-5-(4-ethylthiobenzyl)-2,6-dimethylpyrimidine The title compound was prepared in a similar manner to that described in Example 10 using 5-(4-ethylthiobenzyl)-2,6-dimethyl-3H-pyrimidin-4-one instead of 5-(4-methoxybenzyl)-2,6-dimethyl-3H-pyrimidin-4-one.

$^1$H-NMR (CDCl$_3$) δ ppm: 1.20-1.35 (3H, m), 1.77 (3H, s), 2.01 (3H, s), 2.06 (3H, s), 2.06 (3H, s), 2.40 (3H, s), 2.57 (3H, s), 2.80-2.95 (2H, m), 3.75-4.00 (3H, m), 4.00-4.30 (2H, m), 5.10-5.40 (3H, m), 6.15-6.25 (1H, m), 6.95-7.05 (2H, m), 7.15-7.25 (2H, m)

Reference Example 12

3-(4-Butylbenzyl)-2,6-dimethyl-1H-pyridin-4-one

To a solution of 3-ethoxycarbonyl-2,6-dimethyl-1H-pyridin-4-one (9.7 g) in dichloromethane (200 mL) were added benzyl bromide (8.9 mL) and silver carbonate (41 g), and the mixture was stirred for 2 hours at 50° C. under shading. The reaction mixture was cooled to room temperature, and the insoluble material was removed by filtration. After the filtrate was concentrated under reduced pressure, the residue was purified by column chromatography on silica gel (eluent: hexane/ethyl acetate=1/1) to give 4-benzyloxy-3-ethoxy-carbonyl-2,6-dimethylpyridine (8.6 g). To a solution of the obtained 4-benzyloxy-3-ethoxycarbonyl-2,6-dimethylpyridine (8.6 g) in tetrahydrofuran (60 mL) was added diisobutylaluminum hydride (1.5 mol/L solution in toluene, 50 mL) at 0° C. The temperature was raised to room temperature, and the reaction mixture was stirred for additionally 40 minutes. After the reaction mixture was poured into 2 mol/L hydrochloric acid (68 mL), 2 mol/L aqueous sodium hydroxide solution (130 mL) was added to the mixture, and the mixture was extracted with dichloromethane. The organic layer was dried over anhydrous sodium sulfate, and the solvent was removed under reduced pressure to give 4-benzyloxy-3-hydroxymethyl-2,6-dimethyl-pyridine (7.2 g). To a solution of the obtained 4-benzyloxy-3-hydroxymethyl-2,6-dimethylpyridine (7.2 g) in dichloromethane (120 mL) was added a Dess-Martin reagent (1,1,1-triacetoxy-1,1-dihydro-1,2-benziodoxol-3(1H)-one) (15 g), and the mixture was stirred for 6.5 hours at room temperature. To the reaction mixture were added saturated aqueous sodium bicarbonate solution (150 mL) and 10% sodium thiosulfate (150 mL), and the mixture was extracted with diethyl ether. The organic layer was dried over anhydrous sodium sulfate, and the solvent was removed under reduced pressure. The residue was purified by column chromatography on silica gel (eluent: hexane/ethyl acetate=1/2) to give 4-benzyloxy-3-formyl-2,6-dimethylpyridine (5.3 g). To a solution of 4-butyl-bromobenzene (0.052 g) in tetrahydrofuran (1.2 mL) was added tert-butyllithium (1.5 mol/L solution in hexane, 0.20 mL) at −78° C. under an argon atmosphere, and the mixture was stirred for 30 minutes at the same temperature. To the reaction mixture was added 4-benzyloxy-3-formyl-2,6-dimethylpyridine (0.048 g) in tetrahydrofuran (1.3 mL), and the mixture was stirred for, 50 minutes at 0° C. To the reaction mixture was added saturated aqueous ammonium chloride solution, and the mixture was extracted with diethyl ether. The organic layer was dried over anhydrous sodium sulfate and concentrated under reduced pressure. The residue was purified by preparative thin layer chromatography on silica gel (developing, solvent: hexane/ethyl acetate=1/2) to give 4-benzyloxy-2,6-dimethylpyridin-3-yl 4-butylphenyl methanol (0.043 g). To a solution of the obtained 4-benzyloxy-2,6-dimethylpyridin-3-yl 4-butylphenyl methanol (0.043 g) in ethanol (2.3 mL) was added 10% palladium carbon powder (0.085 g), and the mixture was stirred for 12 hours at room temperature under a hydrogen atmosphere. The insoluble material was removed by filtration, and the filtrate was concentrated under reduced pressure. The residue was purified by preparative thin layer chromatography on silica gel (developing solvent: dichloromethane/methanol=8/1) to give, 3-(4-butylbenzyl)-2,6-dimethyl-1H-pyridin-4-one (0.027 g).

$^1$H-NMR (CDCl$_3$) δ ppm: 0.89 (3H, t, J=7.3 Hz), 1.20-1.35 (2H, m), 1.45-1.60 (2H, m), 2.13 (3H, s), 2.17 (3H, s), 2.49 (2H, t, J=7.7 Hz), 3.83 (2H, s), 6.08 (1H, s), 6.90-7.05 (4H, m), 12.54 (1H, brs)

Example 13

4-(2,3,4,6-tetra-O-acetyl-β-D-glucopyranosyloxy)-3-(4-butyl benzyl)-2,6-dimethylpyridine The title compound was prepared in a similar manner to that described in Example 1 using 3-(4-butylbenzyl)-2,6-dimethyl-1H-pyridin-4-one instead of 6-(N-acetylamino)-3-(4-ethylbenzyl)-1H-pyridin-2-one.

$^1$H-NMR (CDCl$_3$) δ ppm: 0.89 (3H, t, J=7.3 Hz), 1.20-1.40 (2H, m), 1.45-1.60 (2H, m), 1.58 (3H, s), 2.00 (3H, s), 2.06 (3H, s), 2.10 (3H, s), 2.38 (3H, s), 2.45-2.60 (5H, m), 3.75 (1H, d, J=15.7 Hz), 3.90-4.00 (1H, m), 4.06 (1H, d, J=15.7 Hz), 4.15-4.35 (2H, m), 5.05-5.35 (4H, m), 6.68 (1H, s), 6.85-6.95 (2H, m), 6.95-7.10 (2H, m)

Reference Example 13

3-(4-Methoxybenzyl)-1H-pyridin-2-one

To a solution of n-butyllithium (1.57 mol/L solution in tetrahydrofuran, 2.0 mL) in tetrahydrofuran (23 mL) was added 2,2,6,6-tetramethylpyridine (0.57 mL) at −78° C. The temperature was raised to 0° C., and the mixture was stirred for 30 minutes. After the reaction mixture was cooled to −78° C., 2-chloropyrazine (0.22 mL) was added to the reaction mixture, and the mixture was stirred for 1 hour at the same temperature. To the reaction mixture was added 4-methoxybezaldehyde (0.35 mL), and the mixture was stirred for additionally 1.5 hours. To the reaction-mixture were added concentrated hydrochloric acid (1.2 mL), ethanol (1.2 mL) and tetrahydrofuran (4.8 mL), and the temperature was raised to room temperature. To the reaction mixture was added saturated aqueous sodium bicarbonate solution, and the mixture was concentrated under reduced pressure. After the residue was extracted with dichloromethane, the organic layer was dried over anhydrous sodium sulfate, and the solvent was removed under reduced pressure. The residue was purified by column chromatography on silica gel (eluent: hexane/ethyl acetate=3/2) to give 2-chloropyrazin-3-yl 4-methoxyphenyl methanol (0.31 g). To a suspension of the obtained 2-chloropyrazin-3-yl 4-methoxyphenyl methanol(0.13 g), sodium hydroxide (0.12 g) and potassium carbonate (0.072 g) in toluene (1 mL) were added benzyl alcohol (0.080 mL) and tris-[2-(2-methoxyethoxy)ethyl]amine (0.017 mL), and the mixture was stirred for 2 hours at 120° C. To the reaction mixture was added water, and the mixture was extracted with diethyl ether. The organic layer was dried over anhydrous sodium sulfate, and the solvent was removed under reduced pressure. The residue was purified by preparative thin layer chromatography on silica gel (developing solvent: hexane/ethyl acetate=1/1) to give 2-benzyloxy-3-(4-methoxybenzyl)pyrazine (0.026 g). To a solution of the obtained 2-benzyloxy-3-(4-methoxybenzyl)-pyrazine (0.025 g) in ethanol (1 mL) was added 10% palladium carbon powder (0.0099 g), and the mixture was stirred for 2 hours at room temperature under a hydrogen atmosphere. The insoluble material was removed by filtration, and the filtrate was concentrated under reduced pressure. The residue was purified by preparative thin layer chromatography on silica gel (developing solvent: hexane/ethyl acetate=1/3) to give 3-(4-methoxybenzyl)-1H-pyridin-2-one (0.0055 g).

$^1$H-NMR (CDCl$_3$) δ ppm: 3.77 (3H, s), 4.07 (2H, s), 6.80-6.90 (2H, m), 7.09 (1H, d, J=4.1 Hz), 7.20-7.35 (2H, m), 7.39 (1H, d, J=4.1 Hz), 12.75 (1H, brs)

Example 14

2-(2,3,4,6-tetra-O-acetyl-β-D-glucopyranosyloxy)-3-(4-methoxybenzyl)pyrazine

The title compound was prepared in a similar manner to that described in Example 1 using 3-(4-methoxybenzyl)-1H-pyrazin-2-one instead of 6-(N-acetylamino)-3-(4-ethyl-benzyl)-1H-pyridin-2-one.

$^1$H-NMR (CDCl$_3$) δ ppm: 1.89 (3H, s), 2.04 (3H, s), 2.05 (6H, s), 3.76 (3H, s), 3.85-4.00 (1H, m), 4.02 (1H, d, J=14.1 Hz), 4.05-4.15 (2H, m), 4.28 (1H, dd, J=4.5, 12.5 Hz), 5.15-5.45 (3H, m), 6.10 (1H, d, J=8.2 Hz), 6.75-6.85 (2H, m), 7.15-7.25 (2H, m), 7.95 (1H, d, J=2.7 Hz), 8.20 (1H, d, J=2.7 Hz)

Reference Example 14

4-Benzyl-2H-pyridazin-3-one

To a solution of 1-methyl 2-benzylsuccinate (0.78 g) in tetrahydrofuran (12 mL) was added borane tetrahydrofuran complex (0.93 mol/L solution in tetrahydrofuran, 3.8 mL) at 0° C. The temperature was raised to room temperature, and the mixture was stirred for 15 hours. To the reaction mixture were added water and potassium carbonate, and the mixture was extracted with diethyl ether. After the organic layer was washed with water and dried over anhydrous magnesium sulfate, the solvent was removed under reduced pressure. After the residue was dissolved in dichloromethane (20 mL), a Dess-Martin reagent (1,1,1-tri-acetoxy-1,1-dihydro-1,2-benziodoxol-3(1H)-one)(1.2 g), and the mixture was stirred for 2 hours at room temperature. The reaction mixture was poured into water, and the mixture was extracted with diethyl ether. After the organic layer was washed with water and dried over anhydrous magnesium sulfate, the solvent was removed under reduced pressure. After the residue was dissolved in ethanol (5 mL), hydrazine monohydride (0.14 mL) was added to the solution, and the mixture was heated under reflux for 30 minutes. The reaction mixture was poured into water, and the mixture was extracted with ethyl acetate. The organic layer was dried over anhydrous magnesium sulfate, and the solvent was removed under reduced pressure. The residue was purified by column chromatography on silica gel (eluent: hexane/ethyl acetate=2/1-1/1) to give 4-benzyl-3,4-dihydro-2H-pyridazin-3-one (0.31 g). To a solution of the obtained 4-benzyl-3,4-dihydro-2H-pyridazin-3-one (0.16 g) in ethanol (5 mL-) was added selenium dioxide (0.48 g), and the mixture was heated under reflux for 41 hours. The reaction mixture was poured into water, and the mixture was extracted with ethyl acetate. The organic layer was dried over anhydrous magnesium sulfate and concentrated under reduced pressure. To the residue was added diethyl ether, and the resulting precipitated crystals were collected by filtration and dried under reduced pressure to give 4-benzyl-2H-pyridazin-3-one (0.083 g).

$^1$H-NMR (DMSO-d$_6$) δ ppm: 3.77 (2H, s), 7.05 (1H, d, J=4.0 Hz), 7.15-7.40 (5H, m), 7.77 (1H, d, J=4.0 Hz), 13.0 (1H, brs)

Example 15

3-(2,3,4,6-Tetra-O-acetyl-β-D-glucopyranosyloxy)-4-benzyl-pyridazine

The title compound was prepared in a similar manner to that described in Example 1 using 4-benzyl-2H-pyridazin-3-one instead of 6-(N-acetylamino)-3-(4-ethylbenzyl)-1H-pyridin-2-one.

$^1$H-NMR (CDCl$_3$) δ ppm: 1.92 (3H, s), 2.04 (3H, s), 2.06 (3H, s), 2.06 (3H, s), 3.85-3.95 (2H, m), 3.95-4.05 (1H, m), 4.05-4.20 (1H, m), 4.34 (1H, dd, J=4.4, 12.6 Hz), 5.15-5.45 (3H, m), 6.44 (1H, d, J=8.1 Hz), 7.05-7.10 (1H, m), 7.10-7.20 (2H, m), 7.20-7.35 (3H, m), 8.77 (1H, d, J=4.7 Hz)

Example 16

6-(N-Acetylamino)-3-(4-ethylbenzyl)-2-(β-D-glucopyranosyl-oxy)pyridine

The title compound was prepared in a similar manner to that described in Example 6 using 6-amino-2-(2,3,4,6-tetra-O-acetyl-β-D-glucopyranosyloxy)-3-(4-ethylbenzyl)pyridine instead of 2-(2,3,4,6-tetra-O-acetyl-β-D-glucopyranosyl-oxy)-3-[4-(2-methoxymethyloxyethyl)benzyl]-4,6-dimethyl-pyridine.

$^1$H-NMR (CD$_3$OD) δ ppm: 1.20 (3H, t, J=7.6 Hz), 2.13 (3H, s), 2.59 (2H, q, J=7.6 Hz), 3.30-3.60 (4H, m), 3.66 (1H, dd, J=5.6, 11.8 Hz), 3.75-4.00 (3H, m), 5.89 (1H, d, J=7.8 Hz), 7.00-7.20 (4H, m)), 7.35 (1H, d, J=8.2 Hz), 7.62 (1H, brd, J=8.2 Hz)

Example 17

6-Amino-3-(4-ethylbenzyl)-2-(β-D-glucopyranosyloxy)pyridine

The title compound was prepared in a similar manner to that described in Example 6 using 6-amino-2-(2,3,4,6-tetra-O-acetyl-β-D-glucopyranosyloxy)-3-(4-ethylbenzyl)pyridine instead of 2-(2,3,4,6-tetra-O-acetyl-β-D-glucopyranosyl-oxy)-3-[4-(2-methoxymethyloxyethyl)benzyl]-4,6-dimethyl-pyridine.

$^1$H-NMR (CD$_3$OD) δ ppm: 1.19 (3H, t, J=7.6 Hz), 2.58 (2H, q, J=7.6 Hz), 3.30-3.55 (4H, m), 3.60-3.95 (4H, m); 5.75-5.85 (1H, m), 6.12 (1H, d, J=8.0 Hz), 7.00-7.20 (5H, m)

Example 18

3-(4-Ethylbenzyl)-2-(β-D-glucopyranosyloxy)-4,6-dimethyl-pyridine

The title compound was prepared in a similar manner to that described in Example 6 using 2-(2,3,4,6-tetra-O-acetyl-β-D-glucopyranosyloxy)-3-(4-ethylbenzyl)-4,6-dimethyl-pyridine instead of 2-(2,3,4,6-tetra-O-acetyl-β-D-glucopyranosyloxy)-3-[4-(2-methoxymethyloxyethyl)benzyl]-4,6-dimethylpyridine.

¹H-NMR (CD₃OD) δ ppm: 1.17 (3H, t, J=7.5 Hz), 2.17 (3H, s), 2.36 (3H, s), 2.56 (2H, q, J=7.5 Hz), 3.30-3.55 (4H, m), 3.68 (1H, dd, J=5.2, 12.0 Hz), 3.84 (1H, dd, J=2.2, 12.0 Hz), 3.94 (1H, d, J=15.3 Hz), 4.05 (1H, d, J=15.3 Hz), 5.85-5.95 (1H,m), 6.72 (1H, s), 7.00-7.15 (4H, m)

Example 19

2-(β-D-Glucopyranosyloxy)-3-(4-methoxybenzyl)-4,6-dimethyl-pyridine

The title compound was prepared in a similar manner to that described in Example 6 using 2-(2,3,4,6-tetra-O-acetyl-β-D-glucopyranosyloxy)-3-(4-methoxybenzyl)-4,6-dimethyl-pyridine instead of 2-(2,3,4,6-tetra-O-acetyl-β-D-gluco-pyranosyloxy)-3-[4-(2-methoxymethyloxyethyl)benzyl]-4,6-dimethylpyridine.

¹H-NMR (CD₃OD) δ ppm: 2.17 (3H, s), 2.35 (3H, s), 3.30-3.55 (4H, m), 3.68 (1H, dd, J=5.3, 12.0 Hz), 3.72 (3H, s), 3.84 (1H, dd, J=2.2, 12.0 Hz), 3.91 (1H, d, J=15.1 Hz), 4.02 (1H, d, J=15.1 Hz), 5.85-5.95 (1H, m), 6.72 (1H, s), 6.70-6.85 (2H, m), 7.05-7.15 (2H, m)

Example 20

2-(β-D-Glucopyranosyloxy)-3-[4-(2-hydroxyethyl)benzyl]-4,6-dimethylpyridine

To a solution of 2-(β-D-glucopyranosyloxy)-3-[4-(2-methoxymethyloxyethyl)benzyl]-4,6-dimethylpyridine (0.054 g) in dichloromethane (1.2 mL) was trimethylbromosilane (0.061 mL) at −23° C., and the mixture was stirred for 10 minutes. To the reaction mixture was added saturated aqueous sodium bicarbonate solution, and the mixture was extracted with ethyl acetate. The organic layer was dried over anhydrous sodium sulfate, and the solvent was removed under reduced pressure. The residue was purified by preparative thin layer chromatography on silica gel (developing solvent: dichloromethane/methanol=6/1) to give 2-(β-D-glucopyranosyloxy)-3-[4-(2-hydroxyethyl)benzyl]-4,6-dimethylpyridine (0.008 g).

¹H-NMR (CD₃OD) δ ppm: 2.17 (3H, s), 2.36, (3H, s), 2.74 (2H, t, J=7.1 Hz), 3.30-3.60 (4H, m), 3.60-3.75 (3H, m), 3.83 (1H, dd, J=2.3, 12.1 Hz), 3.94 (1H, d, J=15.5 Hz), 4.06 (1H, d, J=15.5 Hz), 5.85-5.95 (1H, m), 6.72 (1H, s), 7.00-7.20 (4H, m)

Example 21

2-(β-D-Glucopyranosyloxy)-6-methoxy-3-(4-methoxybenzyl)-4-methylpyridine

The title compound was prepared in a similar manner to that described in Example 6 using 2-(2,3,4,6-tetra-O-acetyl-β-D-glucopyranosyloxy)-6-methoxy-3-(4-methoxybenzyl)-4-methylpyridine instead of 2-(2,3,4,6-tetra-O-acetyl-β-D-glucopyranosyloxy)-3-[4-(2-methoxymethyloxyethyl)benzyl]-4,6-dimethylpyridine.

¹H-NMR (CD₃OD) δ ppm: 2.15 (3H, s), 3.30-3.55 (4H, m), 3.67 (1H, dd, J=5.5, 12.1 Hz), 3.72 (3H, s), 3.80-3.90 (5H, m), 3.90-4.05 (1H, m), 5.80-5.90 (1H, m), 6.26 (1H,s), 6.70-6.80 (2H, m), 7.05-7.15 (2H, m)

Example 22

4-(4-Ethoxybenzyl)-3-(β-D-glucopyranosyloxy)pyridine

The title compound was prepared in a similar manner to that described in Example 6 using 3-(2,3,4,6-tetra-O-acetyl-β-D-glucopyranosyloxy)-4-(4-ethoxybenzyl)pyridine instead of 2-(2,3,4,6-tetra-O-acetyl-β-D-glucopyranosyloxy)-3-[4-(2-methoxymethyloxyethyl)benzyl]-4,6-dimethylpyridine.

¹H-NMR (CD₃OD) δ ppm: 1.36 (3H, t, J=6.9 Hz), 3.30-3.60 (4H, m), 3.71 (1H, dd, J=5.6, 12.2 Hz),3.89 (1H, dd, J=2.1, 12.2 Hz), 3.95-4.10. (4H, m), 4.99 (1H, d, J=7.6 Hz),6.75-6.90 (2H, m), 7.08 (1H, d, J=5.2 Hz), 7.10-7.20 (2H, m), 8.08 (1H, d, J=5.2 Hz), 8.39 (1H, s)

Example 23

2-(β-D-Glucopyranosyloxy)-3-(4-methoxybenzyl)pyridine

The title compound was prepared in a similar manner to that described in Example 6 using 2-(2,3,4,6-tetra-O-acetyl-β-D-glucopyranosyloxy)-3-(4-methoxybenzyl)pyridine instead of 2-(2,3,4,6-tetra-O-acetyl-β-D-glucopyranosyloxy)-3-[4-(2-methoxymethyloxyethyl)benzyl]-4,6-dimethylpyridine.

¹H-NMR (CD₃OD) δ ppm: 3.35-3.60 (4H, m), 3.69 (1H, dd, J=4.9, 12.1 Hz), 3.76 (3H, s), 3.80-4.00 (3H, m), 5.87 (1H, d, J=7.6 Hz), 6.80-6.90 (2H, m), 6.93 (1H, dd, J=5.0, 7.3 Hz), 7.10-7.20 (2H, m), 7.30-7.45 (1H, m), 7.97 (1H, dd, J=1.6, 5.0 Hz)

Example 24

4-7(β-D-Glucopyranosyloxy)-5-(4-methoxybenzyl)-2,6-dimethyl-pyrimidine

To a solution of 4-(2,3,4,6-tetra-O-acetyl-β-D-glucopyranosyloxy)-5-(4-methoxybenzyl)-2,6-dimethylpyrimidine (0.24 g) in methanol (4 mL) was added sodium methoxide (28% solution in methanol, 0.040 mL), and the mixture was stirred for 50 minutes at room temperature. After the reaction mixture was concentrated under reduced pressure, the residue was purified by column chromatography on silica gel (eluent: dichloro-methane/methanol=7/1) to give 4-(β-D-glucopyranosyloxy)-5-(4-methoxybenzyl)-2,6-dimethylpyrimidine (0.11 g).

¹H-NMR (CD₃OD) δ ppm: 2.34 (3H, s), 2.52 (3H, s), 3.30-3.55 (4H, m), 3.68 (1H, dd, J=5.5, 11.9 Hz), 3.73 (3H, s), 3.85 (1H, dd, J=2.1, 11.9 Hz), 3.90 (1H, d, J=15.1 Hz), 4.00 (1H, d, J=15.1 Hz), 6.00-6.10 (1H, m), 6.75-6.85 (2H, m), 7.05-7.15 (2H, m)

Example 25

3-(β-D-Glucopyranosyloxy)-4-[4-(2-hydroxyethyl)benzyl]-pyridine

To a solution of 3-(2,3,4,6-tetra-O-acetyl-β-D-glucopyranosyloxy)-4-[4-(2-benzoyloxyethyl)benzyl]pyridine (0.086 g) in methanol (1 mL) was added sodium methoxide (28% solution in methanol, 0.008 mL), and the mixture was stirred for 23 hours at 25° C. After the reaction mixture was concentrated under reduced pressure, the residue was purified by column chromatography on silica gel (eluent: dichloromethane/methanol=4/1) to give 3-(β-D-glucopyranosyloxy)-4-[4-(2-hydroxy-ethyl)benzyl]pyridine (0.044 g).

¹H-NMR (CD₃OD) δ ppm: 2.78 (2H, t, J=7.2 Hz), 3.30-3.60 (4H, m), 3.60-3.80 (3H, m), 3.89 (1H, dd, J=2.0, 12.2 Hz), 4.03 (1H, d, J=15.1 Hz), 4.11 (1H, d, J=15.1 Hz), 4.99(1H, d, J=7.6 Hz), 7.09 (1H, d, J=5.0 Hz), 7.10-7.25 (4H, m), 8.08 (1H, d, J=5.0 Hz), 8.39 (1H, s)

Example 26

5-(4-Ethylthiobenzyl)-4-(β-D-glucopyranosyloxy)-2,6-dimethylpyrimidine

The title compound was prepared in a similar manner to that described in Example 24 using 4-(2,3,4,6-tetra-O-acetyl-β-D-glucopyranosyloxy)-5-(4-ethylthiobenzyl)-2,6-dimethyl-pyrimidine instead of 4-(2,3,4,6-tetra-O-acetyl-β-D-gluco-pyranosyloxy)-5-(4-methoxybenzyl)-2,6-dimethylpyrimidine.

$^1$H-NMR (CD$_3$OD) δ ppm: 1.23 (3H, t, J=7.3 Hz), 2.34 (3H, s), 2.52 (3H, s), 2.87 (2H, q, J=7.3 Hz), 3.30-3.60.(4H, m), 3.69 (1H, dd, J=5.2, 12.1 Hz), 3.85 (1H, dd, J=2.2, 12.1 Hz), 3.93 (1H, d, J=15.5 Hz), 4.02 (1H, d, J=15.5 Hz), 6.00-6.10 (1H,m), 7.10-7.30 (4H, m)

Example 27

3-(4-Butylbenzyl)-4-(β-D-glucopyranosyloxy)-2,6-dimethyl-pyridine

The title compound was prepared in a similar manner to that described in Example 6 using 4-(2,3,4,6-tetra-O-acetyl-β-D-glucopyranosyloxy)-3-(4-butylbenzyl)-2,6-dimethyl-pyridine instead of 2-(2,3,4,6-tetra-O-acetyl-p-D-glucopyranosyloxy)-3-[4-(2-methoxymethyloxyethyl)benzyl]-4,6-dimethylpyridine.

$^1$H-NMR (CD$_3$OD) δ ppm: 0.91 (3H, t, J=7.3 Hz), 1.25-1.40 (2H, m), 1.45-1.60 (2H, m), 2.37 (3H, s), 2.47 (3H, s), 2.50-2.60 (2H, m), 3.30-3.60 (4H, m), 3.68 (1H, dd, J=6.2, 12.1 Hz), 3.91 (1H, dd, J=2.1, 12.1 Hz), 3.94 (1H, d, J=15.4 Hz), 4.15(1H, d, J=15.4 Hz), 5.05-5.15 (1H; m), 6.95-7.10 (5H, m)

Example 28

2-(β-D-Glucopyranosyloxy)-3-(4-methoxybenzyl)pyrazine

The title compound was prepared in a similar manner to that described in Example 6 using 2-(2,3,4,6-tetra-O-acetyl-β-D-glucopyranosyloxy)-3-(4-methoxybenzyl)pyrazine instead of 2-(2,3,4,6-tetra-O-acetyl-β-D-glucopyranosyloxy)-3-[4-(2-methoxymethyloxyethyl)benzyl]-4,6-dimethylpyridine.

$^1$H-NMR (CD$_3$OD) δ ppm: 3.35-3.60 (4H, m), 3.66 (1H, dd, J=4.8, 12.1 Hz), 3.74 (3H, s), 3.81 (1H, dd, J=1.9, 12.1 Hz), 4.06 (1H, d, J=14.2 Hz), 4.17 (1H, d, J=14.2 Hz), 5.89 (1H, d, J=8.0 Hz), 6.75-6.85 (2H,m), 7.15-7.30 (2H, m), 8.03 (1H, d, J=2.8 Hz), 8.10 (1H, d, J=2.8 Hz)

Example 29

4-Benzyl-3-(β-D-Glucopyranosyloxy)pyridazine

To a solution of 3-(2,3,4,6-tetra-O-acetyl-β-D-glucopyranosyloxy)-4-benzylpyridazine (0.055 g) in methanol (2 mL) was added sodium methoxide (28% solution in methanol, 0.010 mL), and the mixture was stirred for 30 minutes at room temperature. After the reaction mixture was concentrated under reduced pressure, the residue was purified by column chromatography on silica gel (eluent: dichloromethane/methanol=7/1) to give 4-benzyl-3-(β-D-Glucopyranosyloxy)pyridazine (0.032 g).

$^1$H-NMR (CD$_3$OD) δ ppm: 3.30-3.65 (4H, m), 3.71 (1H, dd, J=5.0, 12.1 Hz), 3.84 (1H, dd, J=1.5, 12.1 Hz), 3.95-4.10 (2H, m), 6.09 (1H,: d, J=8.2 Hz), 7.15-7.40 (6H, m), 8.70 (1H, d, J=4.7 Hz)

Example 30

3-(4-Methoxybenzyl)-2-(6-O-methoxycarbonyl-β-D-gluco-pyranosyloxy)-4,6-dimethylpyridine To a solution of 2-(β-D-glucopyranosyloxy)-3-(4-methoxy-benzyl)-4,6-dimethylpyridine (0.32 g) in 2,4,6-trimethyl-pyridine (3.8 mL) was added a solution of methyl chloroformate (0.18 mL) in dichloromethane (0.4 mL) at −40° C. The temperature was raised to room temperature, and the mixture was stirred for 7 hours. To the reaction mixture was added 10% aqueous citric acid solution (12 mL), and the mixture was extracted with ethyl acetate. After the organic layer was washed with 10% aqueous citric acid solution and dried over anhydrous sodium sulfate, the solvent was removed under reduced pressure. The residue was purified by column chromatography on silica gel (eluent: ethyl acetate) to give 3-(4-methoxybenzyl)-2-(6-O-methoxy-carbonyl-β-D-glucopyranosyloxy)-4,6-dimethylpyridine (0.27 g).

$^1$H-NMR (CD$_3$OD) δ ppm: 2.15 (3H, s), 2.35 (3H, s), 3.30-3.55 (3H, m), 3.55-3.65 (1H, m), 3.67 (3H, s), 3.72 (3H, s), 3.83 (1H, d, J=15.2 Hz), 4.06 (1H, d, J=15.2 Hz), 4.28 (1H, dd, J=5.7, 11.7 Hz), 4.40 (1H, dd, J=2.1, 11.7 Hz), 5.90-6.00 (1H, m), 6.71 (1H, s), 6.70-6.80 (2H, m), 7.05-7.15 (2H, m)

Test Example 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the PCR reaction using Pfu DNA Polymerase (made by Stratagene), in which the human kidney cDNA library described above was used as the template and the following oligo nucleotides 0702F and 0712R, presented as Sequence Numbers 1 and 2 respectively, were used as the primers. The amplified DNA fragment was ligated into pCR-Blunt (Invitrogen), a vector for cloning, according to standard method of the kit. The *Escherichia coli* HB101 Competent Cell (made by TOYOBO Co., Ltd.) was transformed according to usual method and then selection of the transformants was performed on the LB agar medium containing 50 μg/mL of kanamycin. After plasmid DNA was extracted and purified from the one of the transformants, amplifying of the DNA fragment coding for human SGLT2 was performed by the PCR reaction using Pfu DNA Polymerase (made by Stratagene), in which the following oligo nucleotides 0714F and 0715R, presented as Sequence Numbers 3 and 4 respectively, were used as the primers. The amplified DNA fragment was digested with restriction enzymes, Xho I and Hind III, and then purified with Wizard Purification System (Promega). This purified DNA fragment was inserted at the corresponding restriction sites of pcDNA3.1 (−) Myc/His—A (Invitrogen), avector for expressing of fusion protein. The *Escherichia coli* HB101 Competent Cell (made by TOYOBO Co., Ltd.) was transformed according to usual method and then selection of the transformant was performed on the LB agar medium containing 100 µg/mL of ampicillin. After plasmid DNA was extracted and purified from this transformant, the base sequence of the DNA fragment inserted at the multi-cloning sites of the vector pcDNA3.1 (−) Myc/His—A was analyzed. This clone had a single base substitution (ATC which codes for the isoleucine-433 was substituted by GTC) compared with the human SGLT2 reported by Wells et al (Am. J. Physiol., Vol. 263, pp. 459-465 (1992)). Sequentially, a clone in which valine is substituted for isoleucine-433 was obtained. This plasmid-vector expressing human SGLT2 in which the peptide presented as Sequence Number 5 is fused to the carboxyl terminal alanine residue was designated KL29.

```
Sequence Number 1    ATGGAGGAGCACACAGAGGC
Sequence Number 2    GGCATAGAAGCCCCAGAGGA
Sequence Number 3    AACCTCGAGATGGAGGAGCACACAGAGGC
Sequence Number 4    AACAAGCTTGGCATAGAAGCCCCAGAGGA
Sequence Number 5    KLGPEQKLISEEDLNSAVDHHHHHH
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 µF, $2\times10^6$ cells of COS-7 cell and 20 µg of KL29 in 500 µL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 µL of this cell suspension was added. After overnight culture at 37° C. under 5% $CO_2$, 125 µL of DMEM medium which is containing 10% of fetal bovine serum (Sanko Jyunyaku), 100 units/mL sodium penicillin G (Gibco-BRL: LIFE TECHNOLOGIES), and 100 µg/mL streptomycin sulfate (Gibco-BRL: LIFE TECHNOLOGIES) was added to each well. These cells were cultured until the next day and then they were used for the measurement of the inhibitory activity against the uptake of methyl-α-D-glucopyranoside.

3) Measurement of the Inhibitory Activity Against the Uptake of methyl-α-D-glucopyranbside After removal of the medium of the COS-7 cells expressing transiently human SGLT2, to each well 200 µL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)aminomethane) was added, and the cells were incubated at 37° C. for 10 minutes. The buffer for uptake measurement was prepared by adding 7 µL of methyl-α-D-(UL14C)glucopyranoside (Amersham Pharmacia Biotech) to 525 µL of the uptake buffer (a pH 7.4 buffer containing 140 mM sodium chloride, 2 mM potassium chloride, 1 mM calcium chloride, 1 mM magnesium chloride, 5 mM methyl-α-D-gluco-pyranoside, 10 mM 2-[4-(2-hydroxyethyl)-1-piperazinyl]ethane sulfonic acid and 5 mM tris(hydroxymethyl)aminomethane) containing a test sample and mixing. For the control, the buffer for measurement without any test compound was prepared. For estimate of the basal uptake in the absence of a test compound and sodium, the buffer for measurement of the basal uptake, which contains 140 mM choline chloride in place of sodium chloride, was prepared similarly. After the pretreatment buffer was removed, 75 µL of the each buffer for measurement was added to each well, and the cells were incubated at 37° C. for 2 hours. After the buffer for measurement was removed, 200 µL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris(hydroxymethyl)aminomethane) was added to each well and immediately removed. After two additional washing, the cells were solubilized by addition of 75 µL of 0.2N sodium hydroxide solution to each well. After the cell lysates were transferred to the PicoPlate (Packard) and 150 µL of MicroScint-40 (Packard) was added to each well, the radioactivity was measured with microplate scintillation counter Top-Count (Packard). The difference in uptake was obtained as 100% value by subtracting the radioactivity in the basal uptake from that in control and then the concentrations at which 50% of uptake were inhibited ($IC_{50}$) were calculated from the concentration-inhibition curve by least square method. The results are shown in the following Table 1.

TABLE 1

| Test compound | $IC_{50}$ (nM) |
|---|---|
| Example 18 | 41 |
| Example 19 | 45 |
| Example 20 | 45 |
| Example 21 | 55 |

INDUSTRIAL APPLICABILITY

The nitrogen-containing heterocyclic derivatives represented by the above general formula (I) of the present invention, pharmaceutically acceptable salts thereof and prodrugs thereof show an excellent hypoglycemic effect by excreting excess glucose into the urine through preventing the reabsorption of glucose at the kidney because they exhibit an excellent inhibitory activity in human SGLT2. The present invention can provide drugs for the prevention or treatment of a disease associated with hyperglycemia such as diabetes, diabetic complications, obesity or the like. In addition, since compounds represented by the above general formula (II) or (III) or salts thereof are important as intermediates in the production of the nitrogen-containing heterocyclic derivatives represented by the above general formula (I), pharmaceutically acceptable salts thereof and prodrugs thereof, the present compounds can be readily prepared via such compounds.

[Sequence Listing Free Text]
Sequence Number 1: Synthetic DNA primer
Sequence Number 2: Synthetic DNA primer
Sequence Number 3: Synthetic DNA primer
Sequence Number 4: Synthetic DNA primer
Sequence Number 5: Peptide fused to the carboxyl terminal alanine residue of human SGLT2.

What is claimed is:

1. A nitrogen-containing heterocyclic derivative represented by the general formula:

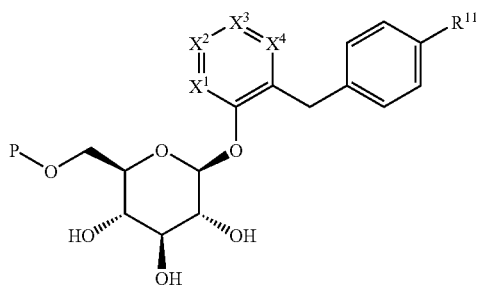

wherein P represents a hydrogen atom or a lower acyl group, a lower alkoxy-substituted (lower acyl) group, a lower alkoxycarbonyl-substituted (lower acyl) group, a lower alkoxycarbonyl group, or a lower alkoxy-substituted (lower alkoxycarbonyl) group; $X^1$ and $X^3$ independently represent N or CH; $X^2$ represents N or $CR^2$; $X^4$ represents N or $CR^3$; and with the proviso that one or two of $X^1$, $X^2$, $X^3$ and $X^4$ represent N; $R^2$ represents a hydrogen atom, a halogen atom, a lower alkyl group, a cyclic lower alkyl group, a lower alkoxy group, an amino group, a (lower acyl)amino group, a mono(lower alkyl)amino group or a di(lower alkyl)amino group; $R^3$ represents a hydrogen atom or a lower alkyl group; $R^{11}$ represents a hydrogen atom, a halogen atom, a lower alkyl group, a lower alkoxy group, a lower alkylthio group, a lower alkoxy-substituted (lower alkyl) group, a lower alkoxy-substituted (lower alkoxy) group, a lower alkoxy(lower alkoxy)-substituted (lower alkyl) group, a cyclic lower alkyl group, a halo(lower alkyl) group or a group represented by the general formula: $P^1$—O-A- wherein $P^1$ represents a hydrogen atom or a lower acyl group, a lower alkoxy-substituted (lower acyl) group, a lower alkoxycarbonyl-substituted (lower acyl) group, a lower alkoxycarbonyl group, or a lower alkoxy-substituted (lower alkoxycarbonyl) group; and A represents a lower alkylene group, a lower alkyleneoxy group or a lower alkylenethio group, or a pharmaceutically acceptable salt thereof.

2. A nitrogen-containing heterocyclic derivative represented by the general formula:

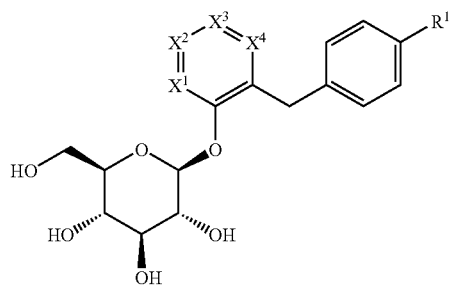

wherein $X^1$ and $X^3$ independently represent N or CH; $X^2$ represents N or $CR^2$; $X^4$ represents N or $CR^3$; and with the proviso that one or two of $X^1$, $X^2$, $X^3$ and $X^4$ represent N; $R^1$ represents a hydrogen atom, a halogen atom, a lower alkyl group, a lower alkoxy group, a lower alkylthio group, a lower alkoxy-substituted (lower alkyl) group, a lower alkoxy-substituted (lower alkoxy) group, a lower alkoxy (lower alkoxy)-substituted (lower alkyl) group, a cyclic lower alkyl group, a halo(lower alkyl) group or a group represented by the general formula: HO-A- wherein A represents a lower alkylene group, a lower alkyleneoxy group or a lower aikylenethio group; $R^2$ represents a hydrogen atom, a halogen atom, a lower alkyl group, a cyclic lower alkyl group, a lower alkoxy group, an amino group, a (lower acyl)amino group, a mono(lower alkyl)amino group or a di(lower alkyl)amino group; and $R^3$ represents a hydrogen atom or a lower alkyl group, or a pharmaceutically acceptable salt thereof.

3. A nitrogen-containing heterocyclic derivative as claimed in claim 1 wherein at least one of P or $R^{11}$ has a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group, or a pharmaceutically acceptable salt thereof.

4. A pharmaceutical composition comprising as an active ingredient a nitrogen-containing heterocyclic derivative as claims in any one of claims 1, 2, or 3, or a pharmaceutically acceptable salt thereof.

5. A method for the treatment of diabetes, diabetic complications, obesity, hyperinsulinemia, glucose metabolism disorders, hyperlipidemia, hypercholesterolemia, hypertriglyceridemia, lipid metabolism disorders, atherosclerosis, hypertension, congestive heart failure, edema, hyperuricemia or gout, which comprises administering to a patient in need thereof an effective amount of a nitrogen-containing heterocyclic derivative as claimed in any one of claims 1, 2, or 3 or a pharmaceutically acceptable salt thereof.

6. A method for the manufacture of a pharmaceutical composition for the treatment of diabetes, diabetic complications, obesity, hyperinsulinemia, glucose metabolism disorders, hyperlipidemia, hypercholesterolernia, hypertriglyceridemia, lipid metabolism disorders, atherosclerosis, hypertension, congestive heart failure, edema, hyperuricemia or gout, which comprises combining the nitrogen-containing heterocyclic derivative as claimed in any one of claims 1, 2 or 3 with a pharmaceutically acceptable additive.

7. A nitrogen-containing heterocyclic derivative represented by the

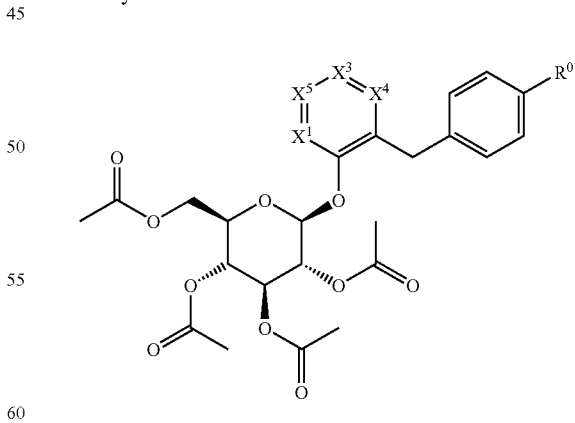

general formula:
wherein $X^1$ and $X^3$ independently represent N or CH; $X^4$ represents N or $CR^3$; $X^5$ represents N or $CR^4$; and with the proviso that one or two of $X^1$, $X^3$, $X^4$ and $X^5$ represent N; $R^0$ represents a hydrogen atom, a halogen atom, a lower alkyl group, a lower alkoxy group, a lower alkylthio group, or a lower alkoxy-substituted (lower alkyl) group, a lower alkoxy-substituted (lower alkoxy) group, a lower alkoxy(lower alkoxy)-substituted (lower alkyl) group, a cyclic lower alkyl group, a halo(lower alkyl) group or a group represented by the general formula: $P^{10}$—O-A- wherein $P^{10}$ represents a hydrogen atom or a hydroxy-protective group; and A represents a lower alkylene group, a lower alkyleneoxy group or a lower alkylenethio group; $R^3$ represents a hydrogen atom or a lower alkyl group; and $R^4$ represents a hydrogen atom, a halogen atom, a lower alkyl group, a cyclic lower alkyl group, a lower alkoxy group, an amino group which may have a protective group, a (lower acyl)amino group, a mono(lower alkyl) amino group which may have a protective group or a di(lower alkyl)amino group, or a salt thereof.

* * * * *